US012611203B2

(12) United States Patent
Welti et al.

(10) Patent No.: US 12,611,203 B2
(45) Date of Patent: Apr. 28, 2026

(54) BIOPSY CARRIER

(71) Applicant: CUTISS AG, Schlieren (CH)

(72) Inventors: Astrid Welti, Stetten (CH); Claude Holenstein, Zurich (CH); Vincent Ronfard, Villarzel (CH); Anna-Lena Dittrich, Zumikon (CH); Reto Frei, Turgi (CH); Christian Wullschleger, Zürich (CH); Sebastian Wollmann, Nussbaumen (CH)

(73) Assignee: CUTISS AG, Schlieren (CH)

( * ) Notice: Subject to any disclaimer, the term of this patent is extended or adjusted under 35 U.S.C. 154(b) by 1181 days.

(21) Appl. No.: 17/616,630

(22) PCT Filed: Jun. 3, 2020

(86) PCT No.: PCT/IL2020/050614
§ 371 (c)(1),
(2) Date: Dec. 3, 2021

(87) PCT Pub. No.: WO2020/245818
PCT Pub. Date: Dec. 10, 2020

(65) Prior Publication Data
US 2022/0225969 A1     Jul. 21, 2022

Related U.S. Application Data

(60) Provisional application No. 62/856,853, filed on Jun. 4, 2019.

(51) Int. Cl.
*A61B 10/00* (2006.01)
*B01L 1/02* (2006.01)
(Continued)

(52) U.S. Cl.
CPC .......... *A61B 10/0096* (2013.01); *B01L 1/025* (2013.01); *B01L 3/5021* (2013.01);
(Continued)

(58) Field of Classification Search
None
See application file for complete search history.

(56) References Cited

U.S. PATENT DOCUMENTS 6,899,850 B2   5/2005   Haywood et al.
9,908,113 B2   3/2018   Sloan et al.
(Continued)

FOREIGN PATENT DOCUMENTS

CA        3062311 A1   11/2018
EP        1599125 B1   8/2013
(Continued)

OTHER PUBLICATIONS

PCT International Search Report and Written Opinion, PCT Application No. PCT/IL2020/050614, Sep. 9, 2020, 37 pages.
(Continued)

*Primary Examiner* — Brittany I Fisher
(74) *Attorney, Agent, or Firm* — Fenwick & West LLP

(57) ABSTRACT

The present invention relates to a device adapted to facilitate transport of a biopsy sample from a sterile extraction site to laboratory-type equipment by which the biopsy sample is processed, while maintaining the biopsy sample wetted and sterile and automatically transferring the biopsy sample from the device to the laboratory-type equipment.

15 Claims, 29 Drawing Sheets

C-C

(51) Int. Cl.

| | |
|---|---|
| *B01L 3/00* | (2006.01) |
| *G01N 1/00* | (2006.01) |
| *G01N 1/06* | (2006.01) |
| *G01N 1/28* | (2006.01) |

(52) U.S. Cl.
CPC ................. *G01N 1/06* (2013.01); *G01N 1/28* (2013.01); *B01L 2200/18* (2013.01); *B01L 2400/049* (2013.01); *G01N 2001/002* (2013.01); *G01N 2001/061* (2013.01)

(56) References Cited

U.S. PATENT DOCUMENTS

| | | | |
|---|---|---|---|
| 2007/0183974 A1* | 8/2007 | Pearlman | .............. C12M 45/02 |
| | | | 424/9.1 |
| 2014/0308164 A1 | 10/2014 | Wilkinson et al. | |

FOREIGN PATENT DOCUMENTS

| | | | | |
|---|---|---|---|---|
| EP | 2896685 A1 | 7/2015 | | |
| WO | WO 2004/075740 A1 | 9/2004 | | |
| WO | WO-2004075719 A2 * | 9/2004 | ......... | A61B 10/0275 |

OTHER PUBLICATIONS

Extended European Search Report, European Patent Office Application No. 20818191.7, mailing date Jun. 16, 2023, 9 pages.

\* cited by examiner

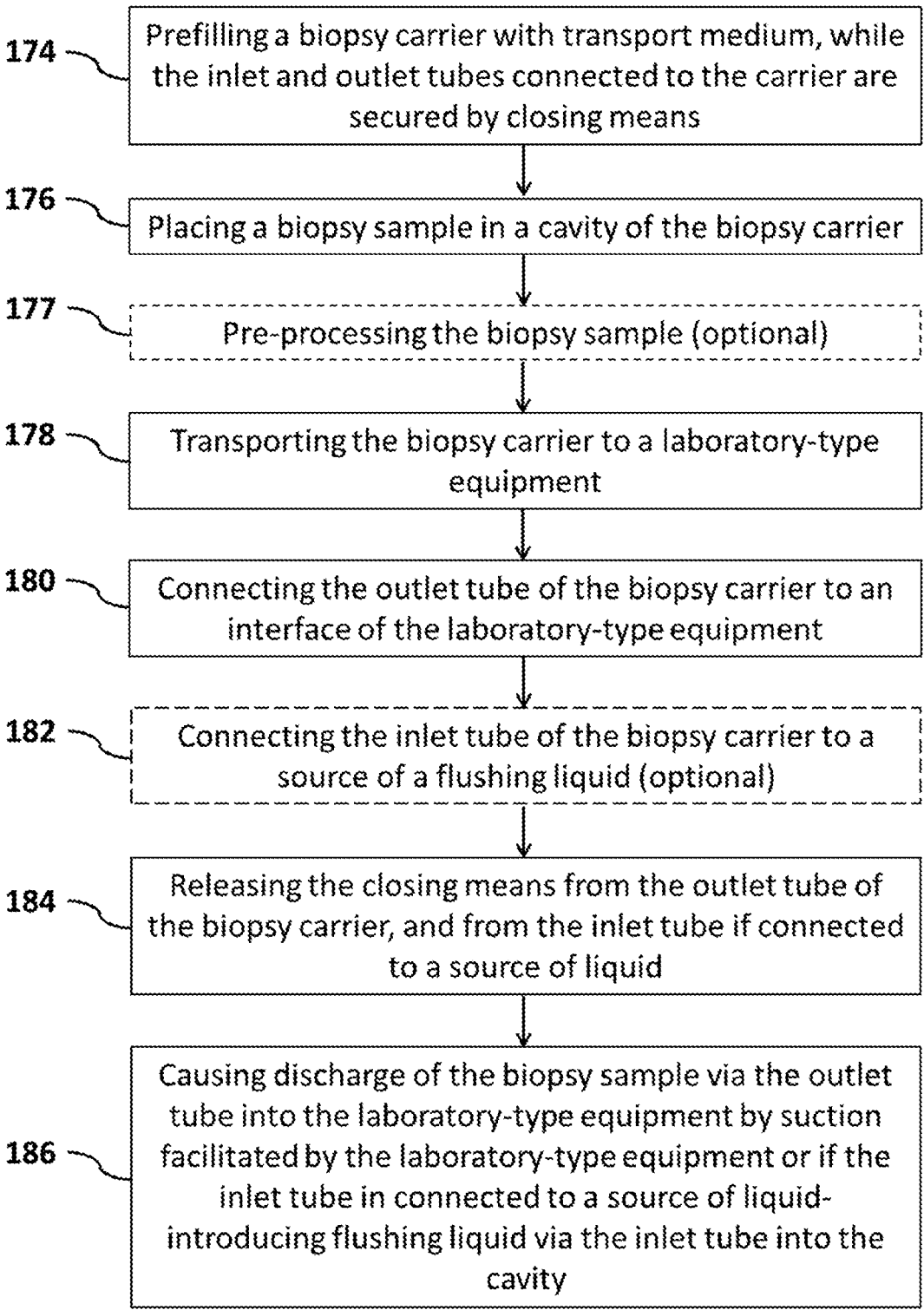

174 — Prefilling a biopsy carrier with transport medium, while the inlet and outlet tubes connected to the carrier are secured by closing means 176 — Placing a biopsy sample in a cavity of the biopsy carrier 177 — Pre-processing the biopsy sample (optional)

178 — Transporting the biopsy carrier to a laboratory-type equipment

180 — Connecting the outlet tube of the biopsy carrier to an interface of the laboratory-type equipment 182 — Connecting the inlet tube of the biopsy carrier to a source of a flushing liquid (optional)

184 — Releasing the closing means from the outlet tube of the biopsy carrier, and from the inlet tube if connected to a source of liquid 186 — Causing discharge of the biopsy sample via the outlet tube into the laboratory-type equipment by suction facilitated by the laboratory-type equipment or if the inlet tube in connected to a source of liquid-introducing flushing liquid via the inlet tube into the cavity

BIOPSY CARRIER

FIELD OF THE INVENTION

The present invention relates to the field of devices for handling tissue samples. More particularly, the invention relates to a device adapted to facilitate transport of a viable biopsy sample from a sterile extraction site whereat it is extracted from the patient to laboratory-type equipment by which the biopsy sample is processed.

BACKGROUND OF THE INVENTION

Skin grafts have become more common and useful in recent years, particularly for the treatment of burns as well as other skin lesions. However, the limiting factor in an efficient treatment, particularly where large affected areas exists on the patient's body, is the ability to supply a suitably large skin graft. As will be apparent to the skilled person, the best skin graft will always be made of the patient's own skin. However, when the affected area is large, this presents a challenge, because only relatively small skin areas can be removed from a patient, to be grafted at a different location on his body.

Attention has been paid in recent times to growing larger autologous skin grafts in the laboratory, using the patient's own skin as a precursor. Doing so involves taking a biopsy of the patient's skin and processing it in the laboratory by a variety of methods, so as to eventually produce a skin graft substantially larger in area than the originally taken biopsy. As a first step in the processing of the biopsy, the skin sample can be cut up into smaller parts, and further processed according to a variety of existing methods.

A substantial problem arises, however in the transferring and handling of the skin biopsy, which may easily become infected and/or otherwise damaged in the course of the transfer from the medical location where the biopsy is taken, to the laboratory which needs to process it, as well as in the process of transferring the biopsy to additional equipment for further processing.

The risk of contamination to a biopsy sample would be significantly reduced if the laboratory equipment by which the biopsy sample is processed would be deployed in the same sterile environment as the location of the biopsy procedure; however, available space in the sterile environment needed by patients and the medical staff for facilitating biopsy and other medical procedures would be compromised.

It is therefore clear that the need exists for a device that obviates the above-identified problems and allows for the safe transferring and handling of the skin biopsy.

It is an object of the present invention to provide such a device.

It is an additional object of the present invention to provide a biopsy carrier from which the biopsy sample is able to be aseptically transferred to laboratory-type equipment by which the biopsy sample is able to be processed.

SUMMARY OF THE INVENTION

In one aspect the present invention provides a biopsy carrier for transporting a biopsy sample, the carrier comprising:

an aseptically closed structure having a cavity prefilled with transport medium;

a selectively sealable and unsealable outlet tube attached to a port in said structure, the port being in fluid communication with the cavity;

wherein, the cavity is configured to receive a biopsy sample such that the biopsy sample is maintained under sterile and wetted conditions while being transported to laboratory-type equipment, thereby maintaining the viability of the biopsy sample; and wherein the biopsy sample is caused to be discharged through the outlet tube to the laboratory-type equipment.

According to some embodiment, the biopsy sample is caused to be discharged through the outlet tube to the laboratory-type equipment by a suction facilitated by the laboratory-type equipment.

According to other embodiments, the biopsy carrier further comprises a selectively sealable and unsealable inlet tube attached to a port in said structure, the port being in fluid communication with the cavity. In one embodiment, the biopsy sample is caused to be discharged through the outlet tube to the laboratory-type equipment is caused by flushing fluid flowable through the inlet tube into the cavity of the biopsy carrier.

According to one embodiment, the biopsy carrier further comprises immobilizing means for protecting the biopsy sample from damage or disfigurement.

According to another embodiment, the biopsy carrier further comprises one or more pre-processing element, for pre-processing the biopsy sample prior to the discharging of the biopsy sample to the laboratory-type equipment. The pre-processing element may be a plurality of blades for cutting the biopsy sample into pieces and/or other pre-processing elements selected from at least one of:

one or more nozzles for introducing liquid to the biopsy sample, wherein the liquid is a washing solution, a disinfecting solution, a solution comprising a reagent or a buffer;

one or more additional ports for introducing liquid to the biopsy sample, wherein the liquid is a washing solution, a disinfecting solution, a solution comprising a reagent or a buffer;

one or more additional ports for extracting liquid from the cavity of the biopsy carrier;

one or more micro-needles for conditioning the surface of the biopsy sample;

one or more sensors for measuring the pH, dissolved oxygen (dO), biochemical compounds and/or the temperature of the liquid inside the cavity;

a bacteria test component; and a transparent part allowing visual contact with the biopsy sample by an imager.

According to a further embodiment, the biopsy carrier further comprises one or more contact elements which, following motion between the one or more contact elements relative to the plurality of blades, are set in pressing contact with both the biopsy sample and the plurality of blades to cause comminution of the biopsy sample and to immobilize the biopsy sample.

In a specific embodiment, the biopsy carrier further comprises a closure carrying the one or more contact elements and which is in releasable engagement with the structure, to occlude aseptically closed cavity; wherein engagement of the closure with the structure causes the one or more contact elements to be set in pressing contact with both the biopsy sample and the plurality of blades.

The biopsy carrier may further comprise a sample support assembly, the sample support assembly comprises:

a blade support, which is recessed with a plurality of blade-receiving slots within each of which is received a corresponding blade of the plurality of blades and with a plurality of spaced apertures, such that each aperture is delimited by one or more blade-receiving slots; and wherein the blade support comprises a plurality of legs extending from the underside of the blade support.

a stripper plate comprising a planar plate in abutting relation with the underside of said blade support, a plurality of blade guards protruding upwards from the planar plate, each blade guard is accommodated in a corresponding aperture in the blade support, and an aperture accommodating the corresponding leg of the blade support;

a force transmitting unit located beneath the stripper plate and comprising a contact plate, which is set in parallel to the stripper plate and the blade support and is in contact with the plurality of legs of the blade support, and a force applier which extends perpendicularly from the underside of the contact; and optionally a blade frame placed in juxtaposition with a corresponding portion of the blade support that is positioned radially outwardly from the apertures formation of the blade support, the blade frame comprising a plurality of spaced grooves, each of which is configured to receive the end of a corresponding blade, and a peripheral curved portion of the same curvature as the peripheral portion of the blade support and aligned therewith;

wherein when no force is transmitted to the force applier, the blade guards extend higher than the plurality of blades and form a grid onto which the biopsy sample is introduced; and wherein when force is transmitted to the force applier, contact plate pushes the blade support by means of the plurality of legs away from the stripper plate in the direction of the transmitted, thus causing the plurality of blades to surpass the plurality of blade guards in height, thereby causing the plurality of blades to cut through the biopsy sample.

In one embodiment the biopsy carrier further comprises a closure and optionally means for displacing the sample support assembly upwardly relative to the structure upon removal of the closure wherein the means for displacing the sample support assembly upwardly relative to the structure comprises a plurality of legs extending from the underside of the planar plate of the stripper plate and chambers configured to receive a corresponding leg of the planar plate; wherein each of the chambers comprises a spring that surrounds the leg of the planar plate; wherein when the closure is engaged with the structure, a compressive force is applied to the plurality of blade guards, which is transmitted to the stripper plate, thereby causing compression of the springs surrounding the legs of the planar plate; and wherein the springs surrounding the legs of the planar plate are extended to cause displacement of the sample support assembly upon removal of the closure. The closure may further comprise one or more contact elements which, following engagement of the closure with the structure, the one or more contact elements are set in pressing contact with both the biopsy sample and the plurality of blade guards to immobilize the biopsy sample and to keep it in wetted condition while being submerged in transport medium.

In some embodiments, the one or more contact elements are a plurality of protrusions formed in a releasable closure, and the plurality of blades are fixed to a body member associated with the structure.

In further embodiments, the closure is provided with two or more guides, and the body member is provided with two or more guide rails, each of the rails adapted to receive a guide slidable therein, and the structure is provided with a thermoplastic elastomer configured to undergo deformation when the closure is engaged with the structure.

According to one embodiment, the biopsy carrier further comprises an additional cover configured to maintain a discharge end of the inlet and outlet tubes in a closed environment.

In specific embodiments, the force that is transmitted to the force applier is manually transmitted, or automatically transmitted by a wirelessly operated piston mechanism located between the bottom of the carrier and force applier.

In another aspect, the present invention provides a method for aseptically transporting a biopsy sample using the biopsy carrier described above, the method comprising:

prefilling the biopsy carrier with transport medium, while the inlet and outlet tubes connected to the biopsy carrier are secured by closing means;

placing a biopsy sample in a cavity of the biopsy carrier;

transporting the biopsy carrier to laboratory-type equipment;

connecting the outlet tube of the biopsy carrier to an interface of the laboratory-type equipment;

releasing the closing means from the outlet tube, thereby opening the tube of the biopsy carrier; and causing the biopsy sample to be discharged via the outlet tube into the laboratory-type equipment.

In one embodiment, causing discharge of the biopsy sample via the outlet tube into the laboratory-type equipment is carried out by suction facilitated by the laboratory-type equipment.

In another embodiment, prior to causing discharge of the biopsy sample via the outlet tube into the laboratory-type equipment, the above method further comprises connecting the inlet tube of the biopsy carrier to a source of a flushing liquid and releasing the closing means from the inlet tube of the biopsy carrier, thereby opening the inlet tube of the biopsy carrier, such that causing discharge of the biopsy sample via the outlet tube into the laboratory-type equipment is carried out by introducing flushing liquid via the inlet tube into the cavity.

In some embodiments, the method further comprises pre-processing the biopsy sample prior to discharging the biopsy sample via the outlet tube into the laboratory-type equipment.

In yet another aspect, there is provided a method for preparing a biopsy sample for subsequent processing operation using the biopsy carrier of the invention, the method comprising:

placing the biopsy sample in the cavity of the biopsy carrier;

immobilizing the biopsy sample by engaging the closure of the biopsy carrier with the structure of the biopsy carrier, thereby;

a. setting the one or more contact elements of the closure in pressing contact with the biopsy sample as well as with the plurality of blades, thereby causing comminution of the biopsy; or b. setting the one or more contact elements of the closure in pressing contact with the biopsy sample as well as with the plurality of blade guards, wherein when the one or more contact elements is set in pressing contact with the biopsy sample as well as with the plurality of blade guards, the method further comprises applying force to the force applier, thereby causing the plurality of blades to cut the biopsy sample into pieces;

connecting the outlet tube of the biopsy carrier to an interface of the laboratory-type equipment and releasing the releasing the closing means from the outlet tube, thereby opening the tube of the biopsy carrier; and causing the biopsy sample to be discharged through the outlet tube of the biopsy carrier into the laboratory-type equipment.

In one embodiment, causing the biopsy sample to be discharged via the outlet tube into the laboratory-type equipment is carried out by suction facilitated by the laboratory-type equipment.

In another embodiment, prior to causing discharge of the biopsy sample via the outlet tube into the laboratory-type equipment, the above method further comprises connecting the inlet tube of the biopsy carrier to a source of a flushing liquid and releasing the closing means from the inlet tube of the biopsy carrier, thereby opening the inlet tube of the biopsy carrier, such that causing discharge of the biopsy sample via the outlet tube into the laboratory-type equipment is carried out by introducing flushing liquid via the inlet tube into the cavity.

All the above characteristics and advantages of the invention will be better understood through the following illustrative description of a specific embodiment thereof.

BRIEF DESCRIPTION OF THE DRAWINGS

In the drawings:

FIG. 1A shows steps in a method for aseptically transferring a biopsy sample from the location of the biopsy procedure to laboratory-type equipment using the biopsy carrier of the invention;

DETAILED DESCRIPTION OF THE INVENTION

Figure 1B:
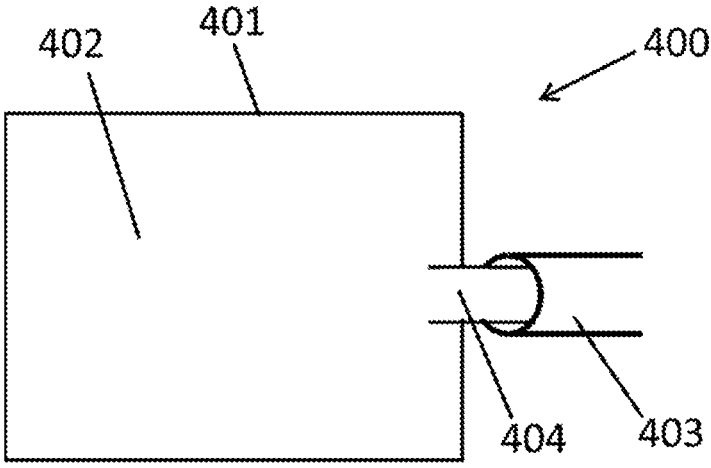
FIG. 1B is a schematic illustration of a biopsy carrier according to an embodiment of the invention, comprising an outlet port and outlet tube.

A biopsy carrier is well suited for facilitating the transport of viable biopsy samples by being configured with a housing that maintains an introduced biopsy sample under sterile and wetted conditions within a prefilled transport medium without being damaged or disfigured while being transported to a laboratory or laboratory-type equipment by which the biopsy sample is able to be processed. The biopsy carrier may also be provided with a grid of blades (or a blade array) or other pre-processing elements and with means for completely discharging the pre-processed biopsy sample to the laboratory-type equipment.

As opposed to prior art methods whereby the container within which the biopsy sample is stored while being transported is opened before being manually transferred to laboratory equipment and being under risk of contamination, the biopsy carrier of the present invention allows the biopsy sample to be discharged and to be transferred directly to the laboratory-type equipment without being exposed to an unsterile environment since the biopsy carrier remains aseptically closed.

The term "aseptically closed" as used herein refers to a structure or cavity that does not allow passage of materials, such as liquids, from or to said structure or cavity. However, the aseptically closed structure or cavity may enable gas exchange between the interior of said structure or cavity with the ambient air for ventilation purposes through ventilation membranes that allow only exchange of gases, but prevent the passage of contaminating agents, such as bacteria, into the closed structure or cavity. Thus, although the aseptically closed structure or cavity is not necessarily completely sealed, said structure or cavity remains sterile. As would be appreciated, a completely sealed structure or cavity is also encompassed by the term "aseptically closed".

As would be appreciated the laboratory-type equipment may be located at the same facility as the place of biopsy extraction or at a laboratory located at a different facility.

The biopsy sample can be maintained viable during transport by the biopsy carrier of the invention for a duration of time of up to one week from the time of the extraction of the biopsy from the patient, assuming the appropriate transport medium and transport conditions (such as temperature) were selected according to the expected duration of the transport.

The term "transport medium" as used herein refers to a solution that is suitable for maintaining a tissue sample viable, such as saline (0.9% NaCl in water), phosphate-buffered saline (PBS) and any conventional cell culture medium, such as Dulbecco's Modified Eagle Medium (DMEM)- or Roswell Park Memorial Institute Medium (RPMI)-based medium, supplemented with one or more of serums, buffers and antibiotics. Of course, the composition of the transport medium is selected according to the time during which the biopsy sample is expected to be in transport. The longer the transport duration, a medium more reach in nutrients and pH buffers should be selected. For example, for a transport duration of up to 1 hour, transport medium in the form of saline or PBS would suffice, while for a longer transport duration, transport media comprising a cell culture medium supplemented as indicated above would be recommended.

During transport, the biopsy carrier can be kept at any temperature suitable for maintaining the biopsy sample viable, for example, the biopsy carrier can be kept at room temperature during short-term transport (such as up to 16 hours), while for longer durations, it is recommended to keep the biopsy carrier at a low temperature, typically about 4° C., by external cooling. Since the device is aseptically closed it can be transported in any cooling environment without compromising its sterility.

The biopsy sample is generally a skin sample that is obtained in a minimally-invasive procedure; however, the biopsy carrier is also capable of handling and transferring other types of biopsy samples under sterile conditions that are obtained invasively or by minimally invasive techniques, such as biopsy samples from liver tissue, kidney tissue, spleen tissue, cornea tissue, bone tissue, tumor tissue and extracts or tissue from the gastrointestinal tract. The biopsy carrier is also capable of handling and transferring other types of human and animal tissue, including connective tissue and small organs present in the body insofar as they have sufficient cohesiveness not to disintegrate in the transport medium.

Broadly speaking, a biopsy sample may be aseptically transported from a sterile environment at the location of the biopsy procedure to laboratory-type equipment using the biopsy carrier of present invention according to the method set forth in FIG. 1A. Firstly, the biopsy carrier is prefilled with liquid transport medium in step 174, while the inlet and outlet tubes connected to the biopsy carrier are securely closed, such as by closing means to prevent leakage of the prefilled transport medium. Then, the biopsy sample is received in the aseptically closed cavity of the biopsy carrier at a sterile environment in step 176. After the biopsy carrier is transported to laboratory-type equipment in step 178, the outlet tube is connected to a suitable interface of the laboratory-type equipment in step 180. Optionally (as indicated by the dashed line in FIG. 1A) the inlet tube is connected to a source of a flushing liquid in step 182. Following release of the previously secured closing means on the outlet tube, thereby opening the outlet tube of the carrier and also of the inlet tube if connected to a source of liquid, in step 184, the biopsy sample is caused to be discharged from the biopsy carrier via the outlet tube and the interface of the laboratory-type equipment in step 186, by vacuum suction facilitated by the laboratory-type equipment or if the inlet tube is connected to a liquid source-introducing flushing liquid via the inlet tube into the cavity.

As the biopsy sample is never exposed to unsterile surroundings while being transported and transferred to the laboratory-type equipment, the risk of contamination to the biopsy sample is precluded.

In an optional step 177 (as indicated by a dashed line in FIG. 1A), the biopsy sample is pre-processed in preparation of the subsequent processing operation. Although step 177 is listed as being performed prior to step 178, it will be appreciated that step 177 can also be performed prior to other steps as well.

It should be noted that the transport medium can also be extracted from the biopsy carrier and further analyzed for its content, for example, in order to comply with regulatory and quality control procedures of a Regulation Authority to analyze the bioburden of the medium (e.g. the sterility of the medium and the presence of mycoplasma).

The term "aseptically transporting" as used herein refers to transporting a biopsy sample, while maintaining said sample under sterile conditions.

The term "closing means" as used herein refers to any means for preventing leakage of the liquids therethrough, such as a clamp and/or a sterile connector, e.g. the genderless CPC AseptiQuik® connector.

Accordingly, the present invention provides a biopsy a biopsy carrier for transporting a biopsy sample as schematically illustrated in FIG. 1B. The biopsy carrier 400 comprises an aseptically closed structure 401 having a cavity 402 prefilled with transport medium. Biopsy carrier also comprises a selectively sealable and unsealable outlet tube 403 attached to a port 404 in said structure, the port being in fluid communication with the cavity.

When biopsy carrier 400 is arrived at the laboratory, it can be sterilely connected to a laboratory-type device, via outlet tube 403 and an interface of the laboratory device. Then, after unsealing the outlet tube, discharge of the biopsy sample is caused be suction facilitated by the laboratory equipment.

Alternatively, the biopsy carrier may also comprise a selectively sealable and unsealable inlet tube attached to a port in the structure of the carrier, the port being in fluid communication with the cavity, such that upon connecting the inlet tube to a source of liquid and unsealing of said inlet tube, discharge of the biopsy sample via the outlet tube connected to an interface of the laboratory-type equipment is caused by introducing a flushing fluid through the inlet tube.

According to one embodiment, the biopsy carrier further comprises immobilizing means for protecting the biopsy sample from damage or disfigurement FIGS. 2A-G schematically illustrate various biopsy carriers, each of which being configured with different integrated pre-processing elements in order to perform a corresponding pre-processing operation for preparing the biopsy sample to be further processed by the laboratory-type equipment. It is envisioned that any one of these biopsy carriers may be configured with more than one of the illustrated pre-processing elements. Each of these biopsy carriers may be configured with an anti-rotation lock, or other means for reducing the risk of unintentionally opening the lid.

Figure 2A:
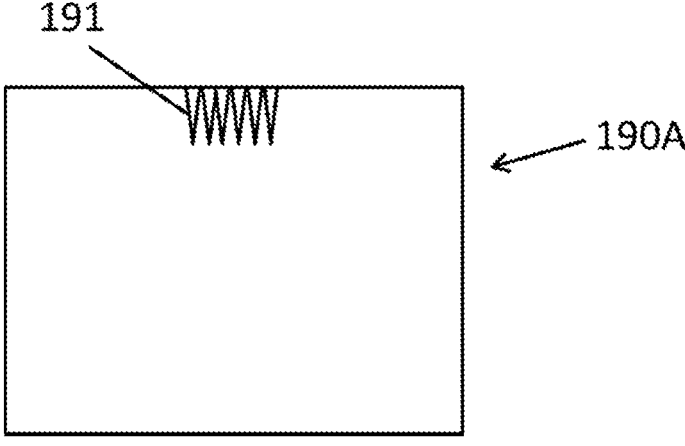
FIG. 2A is a schematic illustration of a biopsy carrier according to an embodiment of the invention, configured with a set of blades.

Biopsy carrier 190A of FIG. 2A is configured with a set of blades 191 for pre-processing the biopsy sample by comminution.

Figure 2B:
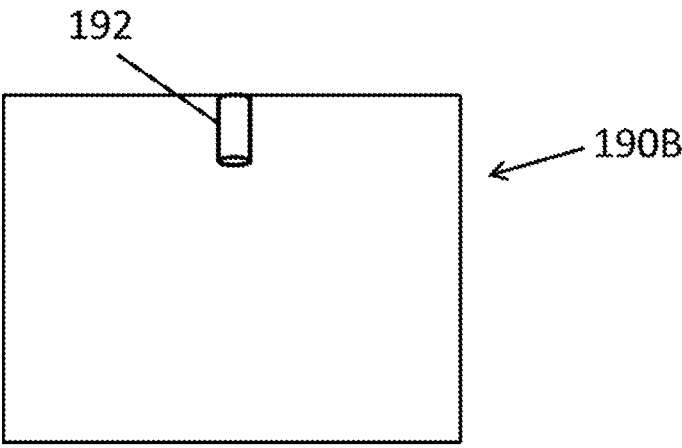
FIG. 2B is a schematic illustration of a biopsy carrier according to an embodiment of the invention, configured with a nozzle.

Biopsy carrier 190B of FIG. 2B is configured with one or more nozzles 192 for washing or disinfecting the biopsy sample, after the inlet port, which is resealable, is connected to a source of washing or disinfecting liquid; alternatively, a reagent or a buffer (such as a wash solution, labeling molecules, antibodies and enzymes) is introducible to the cavity via the nozzle.

Figure 2C:
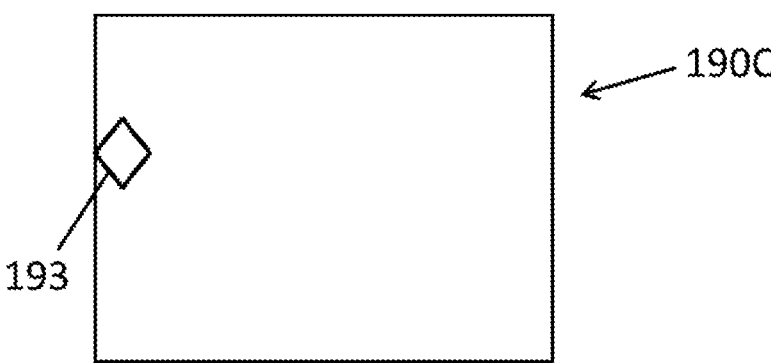
FIG. 2C is a schematic illustration of a biopsy carrier according to an embodiment of the invention, configured with an additional port.

Biopsy carrier 190C of FIG. 2C is configured with an additional port 193, which is resealable, through which a reagent or buffer as described above is introduced or from which sampling media for analysis is extractable.

Figure 2D:
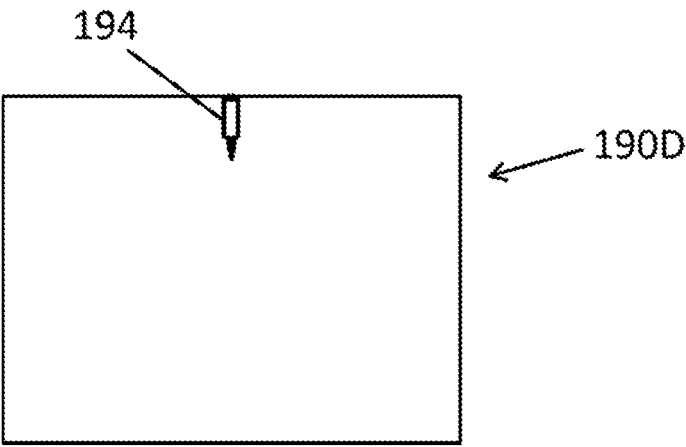
FIG. 2D is a schematic illustration of a biopsy carrier according to an embodiment of the invention, configured with a micro-needle.

Biopsy carrier 190D of FIG. 2D is configured with a micro-needle 194 or an array of micro-needles for conditioning the surface of the biopsy sample.

Figure 2E:
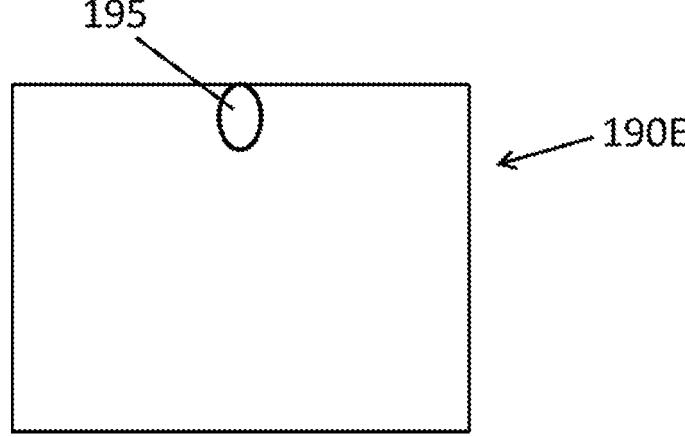
FIG. 2E is a schematic illustration of a biopsy carrier according to an embodiment of the invention, configured with a sensor.

Biopsy carrier 190E of FIG. 2E is configured with a sensor 195, such as a sensor for measuring pH, dissolved oxygen (dO), biochemistry compounds or temperature inside the biopsy carrier. The term "biochemical compounds" refers to compound present in the transport medium during transport that are components in the composition of fresh transport medium, compounds secreted by cells or tissues transported by the biopsy carrier of the invention and metabolites and derivatives thereof. Non-limiting examples of such biochemical compound are carbohydrates (e.g., glucose and lactate), amino acids, pyruvates, bicarbonates, proteins (such as cytokines and enzymes) and reactive oxygen species.

Figure 2F:
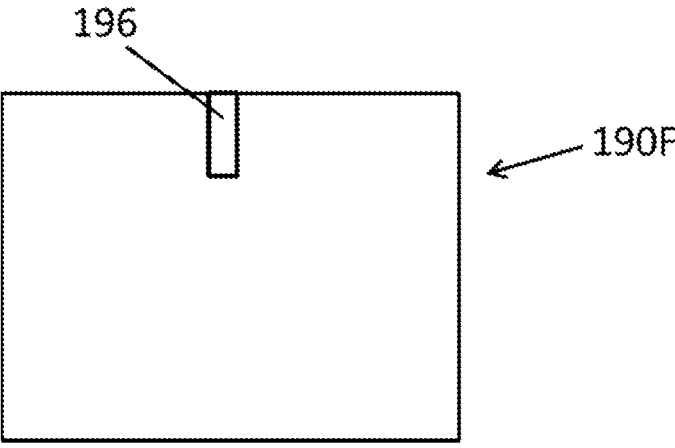
FIG. 2F is a schematic illustration of a biopsy carrier according to an embodiment of the invention, configured with a bacteria test strip.
Figure 2G:
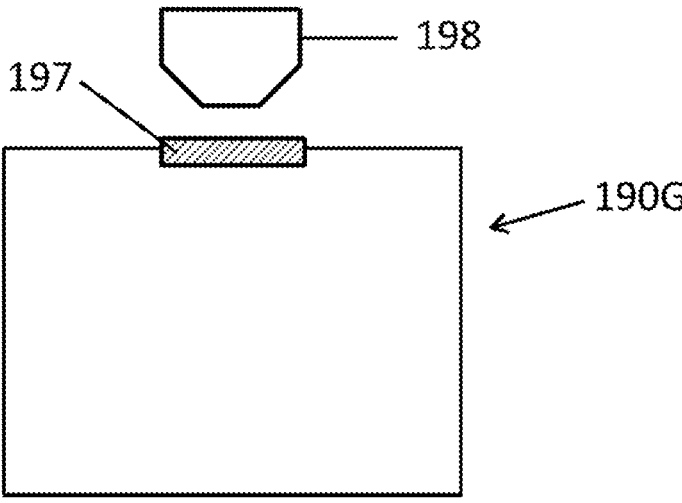
FIG. 2G is a schematic illustration of a biopsy carrier according to an embodiment of the invention, configured with a transparent part allowing visual contact with an imager.

Biopsy carrier 190F of FIG. 2F is configured with a bacteria test strip 196 to rapidly determine whether the biopsy sample has a condition that requires special treatment, such as the presence of methicillin-resistant *Staphylococcus aureus* (MRSA), which is resistant to commonly used antibiotics and therefore requires a specific reagent for its elimination.

Biopsy carrier 190G of FIG. 25G having a transparent part, such as transparent window 197, that allows visual contact with the biopsy sample residing inside the carrier, would enable imaging and/or measuring of the biopsy sample, for example to assess its size or to determine whether it has undergone coloration, by an imager/camera 198 or by other types of monitoring means. It should be noted that measuring the area of the immobilized skin biopsy while inside the carrier, is an important parameter for calculating the amount of reagents, such as enzymes, necessary for processing of the sample within the carrier itself and/or after transferring the biopsy sample to the laboratory-type processing equipment.

The sterile biopsy carrier of the present invention may further comprise immobilizing means to fix the biopsy sample in place during transport or otherwise prevent damage or disfigurement to the biopsy sample. The immobilizing means generally comprise a component that is set in pressing contact with both the biopsy sample and another component usually located at the opposite side of the biopsy sample.

The structure of the biopsy carrier is described with respect to its orientation when capable of receiving and transporting a biopsy sample, for example when a housing member cover is located above the housing member; however, the biopsy carrier may be repositioned to any other orientation without detracting from its functionality as it is configured to ensure that the biopsy sample will remain submerged within the transport medium regardless of the orientation of the biopsy carrier, assuming sufficient media is present.

Reference will now be made to several detailed embodiments of the present invention, examples of which are illustrated in the accompanying figures. Wherever practicable, similar or like reference numbers may be used in the figures and may indicate similar or like functionality. The figures depict embodiments of the present invention for purposes of illustration only. One skilled in the art will readily recognize from the following description that alternative embodiments of the structures illustrated herein may be employed without departing from the principles of the invention described herein.

Figure 3:
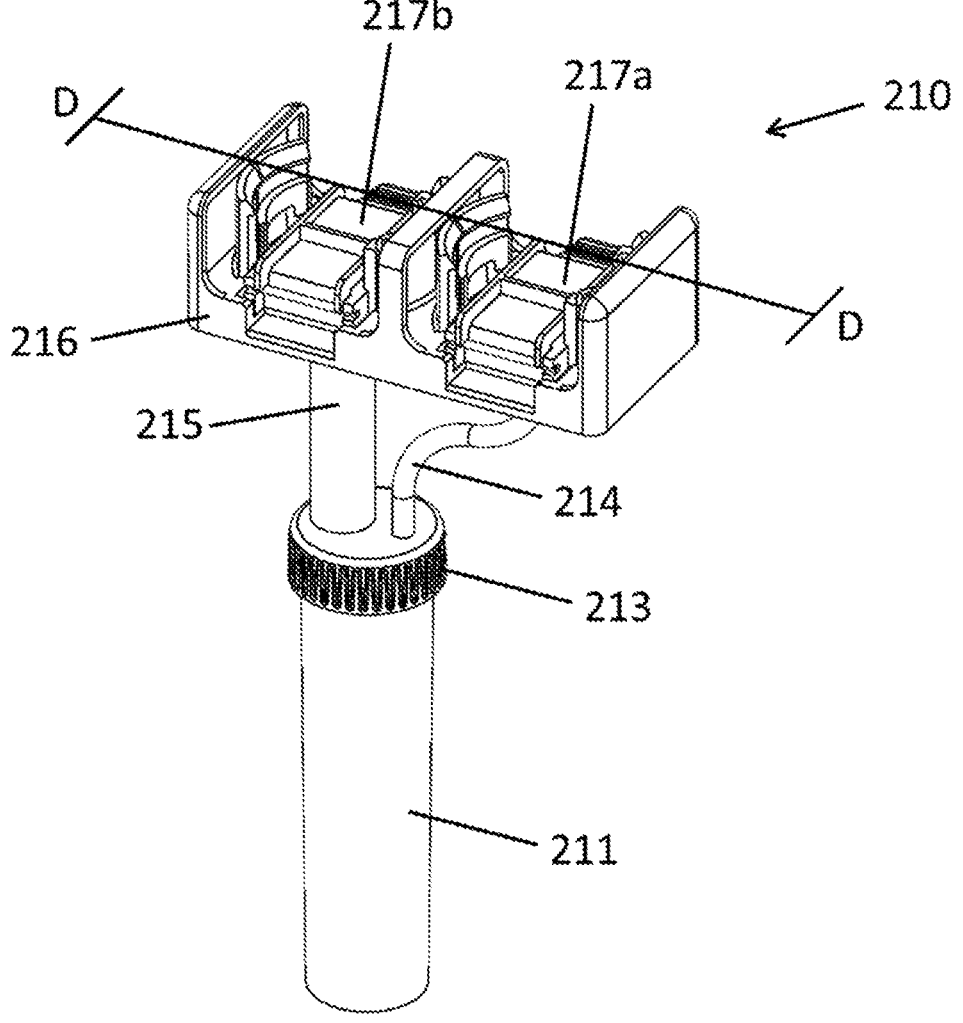
FIG. 3 is a perspective view of a biopsy carrier according to a specific embodiment of the invention.
Figure 4:
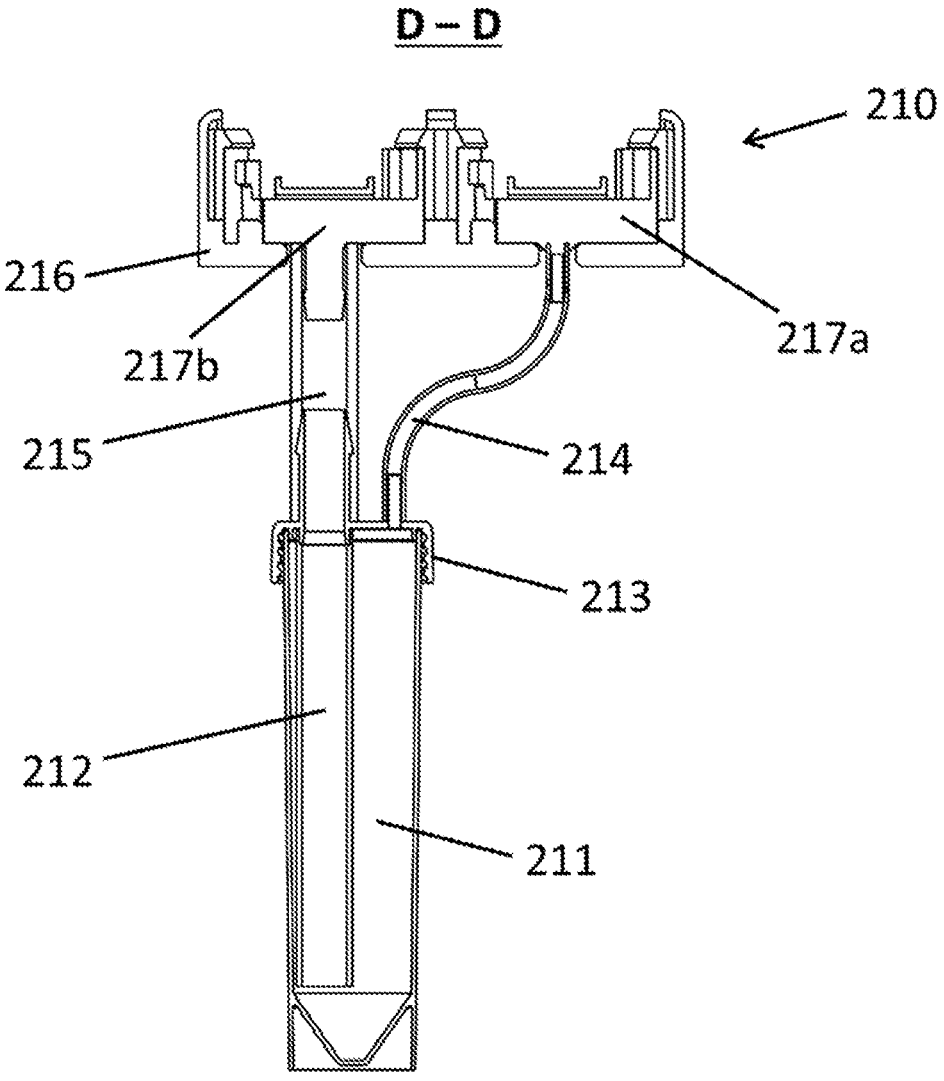
FIG. 4 is a cross sectional view of the carrier of FIG. 3, taken along the D-D plane of FIG. 3.

FIGS. 3 and 4 illustrate an embodiment of a biopsy carrier 210 wherein the biopsy sample is introduced into a tube 211 prefilled with transport medium. Dip tube 212 is positioned within tube 211, such that the bottom end of dip tube 212 is slightly vertically spaced from the bottom of tube 211, so as to be in liquid communication with the interior of centrifuge tube 211. Dip tube 212 facilitates suction-assisted flushing of the biopsy from the biopsy container into a laboratory-type equipment.

Tube 211 may be any commercially available sterile tube, for example, a sterile conical centrifuge tube. In a specific example, tube 211 is a 50 ml centrifuge tube. As would be appreciated, a conical bottom to tube 211 contributes to the sucking effect of the biopsy sample through dip tube 212.

After placing the biopsy sample in tube 211, tube 211 is covered by lid 213, for example by a barbed connection, from which upwardly protrude relatively narrow inlet tube 214, e.g. having a 3.2-mm inner diameter, and a relatively wide exit tube 215, e.g. having a 9.6-mm inner diameter. The upper end of dip tube 212 is positioned at an intermediate region within the interior of exit tube 215, and a sterile connector 217b is in communication with the terminal end of exit tube 215. Sterile connector 217a is in communication with the terminal end of inlet tube 214. Both connectors are able to be removably and separately fixated on stand 216.

When connectors 217a-b are in a released condition and a flushing solution is introduced via connector 217a or a vacuum suction is applied via connector 217b, the biopsy sample is caused to be discharged via exit tube 215 and connector 217b to facilitate sterile transfer of the biopsy sample from the carrier to the laboratory-type equipment.

Figure 5:
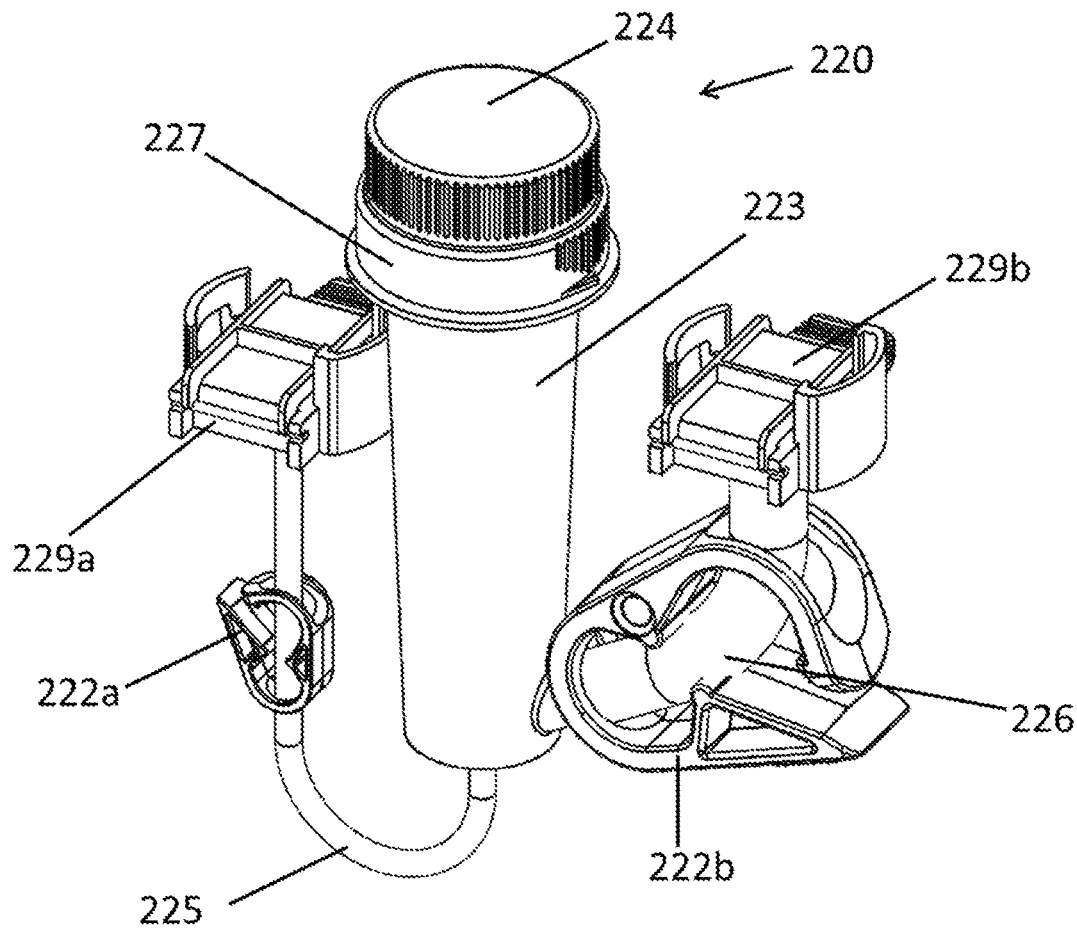
FIG. 5 is a perspective view of a biopsy carrier according to another specific embodiment of the invention.
Figure 6:
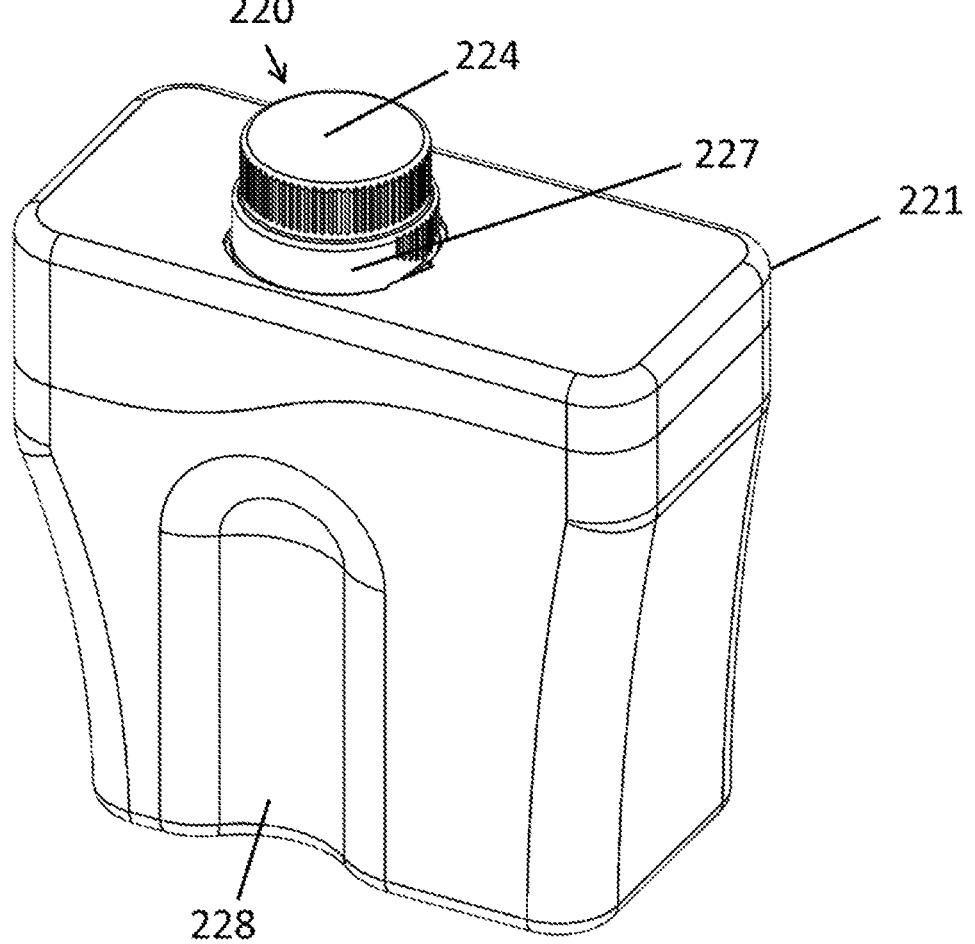
FIG. 6 is a perspective view of the carrier of FIG. 5 fitted in a transport container in a ready for transport state.

FIGS. 5 and 6 illustrate an embodiment of a biopsy carrier 220, which is similar to biopsy carrier 210 of FIGS. 3 and 4, but is configured without a stand. The biopsy sample and transport medium are received in process container 223. Relatively narrow inlet tube 225 terminating with sterile connector 229a protrudes from the bottom of process container 223, and relatively wide exit tube 226 terminating with sterile connector 229b protrudes from the side at the bottom of process container 223. Process container 223 is covered by lid 224 having an anti-rotation lock 227, and is fitted within transport container 221 such that anti-rotation lock 227 and lid 224 protrude upwardly from transport container 221. Transport container 221 may have a basic three dimensional rectangular shape, optionally with niches 228 for enabling better grip of the container by a user.

When connectors 229a-b are in a released condition and a flushing solution is introduced via connector 229a or a vacuum is applied via connector 229b, the biopsy sample is caused to be discharged via exit tube 226 and connector 229b to facilitate sterile transfer of the biopsy sample from the carrier to the laboratory-type equipment.

It should be noted that in order to prevent discharge of the liquid transport medium from the process container 223 during transport, clamps 222a and 222b may be provided on the tubes 225 and 226, respectively.

Figure 7:
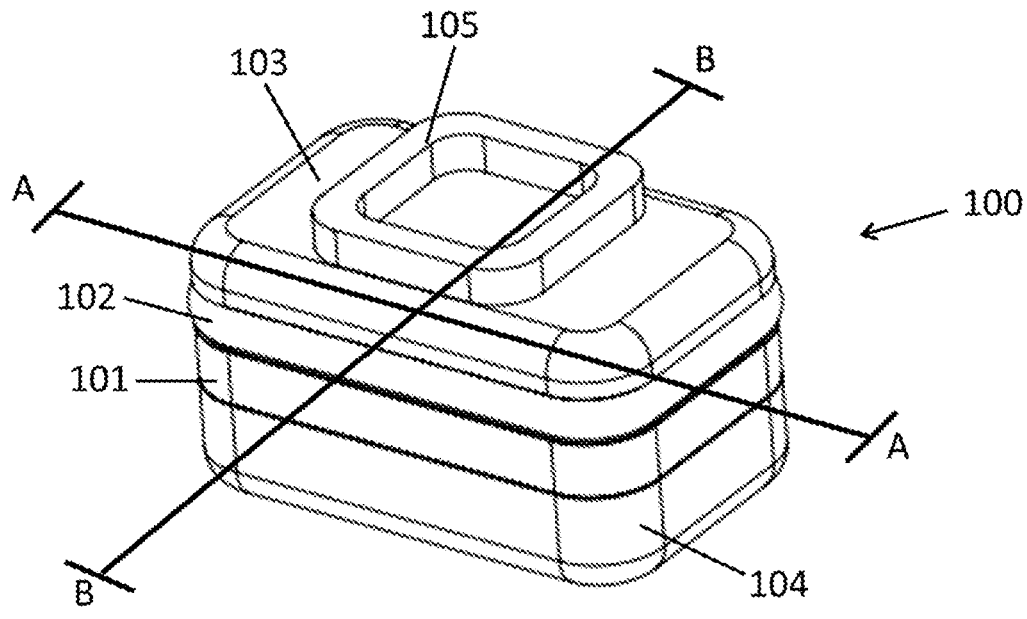
FIG. 7 is a perspective view of a biopsy carrier according to yet another specific embodiment in a closed configuration and ready for transport.

Reference is now made to the embodiment of FIG. 7, which comprises pre-processing elements. Biopsy carrier 100 in the shape of a box has a central section 101, a thermoplastic elastomer section 102, which is a part of central section 101, the purpose of which will be explained below, a top cover 103 and a bottom cover 104. Cover 103 or portions thereof may optionally be made transparent to allow viewing the biopsy sample, once housed in the device.

Figure 8:
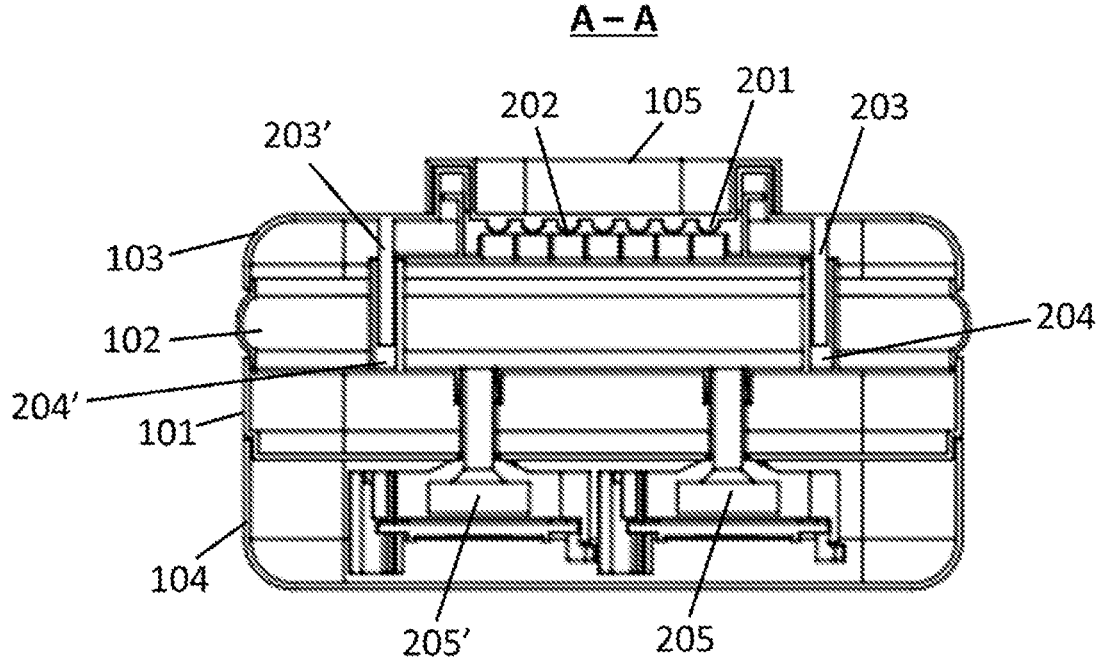
FIG. 8 is a cross-sectional view of the carrier of FIG. 7, taken along the A-A plane of FIG. 7.

The operation of the device and of its various parts will be easily understood by looking at FIG. 8, which shows the interior of the device. The underside of top cover 103 is provided with a plurality of pressure elements in the shape of protrusions or knobs 201, which are designed to come into contact with a plurality of blades 202, associated with central section 101 and located above thermoplastic elastomer section 102. Of course, alternative shapes can be provided for the pressure elements, as long as they fulfill their role of causing the blades to cut the biopsy sample when they apply pressure onto its surface. The biopsy sample is placed on blades 202, which is arranged, according to one embodiment, in a regular grid, and then lid 105 located on the top cover 103 is closed. Once closed, lid 105 is airtight, thus ensuring that the biopsy sample is kept under sterile conditions. Before closing lid 105, the chamber which is located in the interior of the thermoplastic elastomer section 102 and top cover 103 is filled with a transport medium for the purpose of maintaining the biopsy sample in viable conditions during transport. The top cover is provided with guides 203 and 203', which are slidable into guide rails 204 and 204', which are part of central section 101. When pressure is applied on top cover 103, guides 203 and 203' slide into guide rails 204 and 204', thus allowing pressure elements 201 to apply a pressure on the surface of the biopsy sample, thus causing it to be cut into smaller pieces by blades 202 and administered into the medium-filled chamber below. Thermoplastic elastomer band 102 is designed to absorb the displacement of the liquid resulting from the downwards movement of cover 103.

Two sterile fluid connectors, 205 and 205' (e.g., CPC AseptiQuik®) are provided for the purpose of aseptically transferring the comminuted biopsy sample from the device, once it reaches the laboratory-type equipment or once it is set in liquid communication with the laboratory-type equipment, and is connected, via said fluid connectors, to the inlet of the next processing apparatus. As would be appreciated by a skilled artisan, when fluid connectors 205 and 205' are closed, the chamber inside the carrier and the biopsy sample remain sterile. Bottom cover 104 is only removed when it is desired to discharge the comminuted biopsy sample through said fluid connectors 205 and 205'. It should also be noted that in order to prevent discharge of the liquid transport medium from the chamber during transport, a check valve or a clamp may be provided on the tubing that lies between the chamber and the fluid connectors 205 and 205'.

Figure 9:
FIG. 9 is another cross-sectional view of the device of FIG. 7, taken along the B-B plane of FIG. 7.
Figure 9:
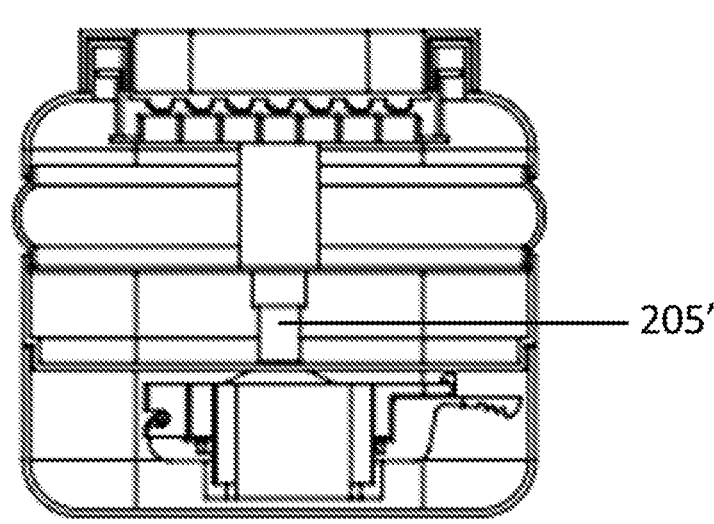

FIG. 9 shows the device of FIG. 7 in a cross-sectional lateral view taken along the B-B plane, with fluid connector 205' partially seen.

FIGS. 10-28 and 30-32 illustrate another embodiment of a biopsy carrier which is configured to prevent spillage of the liquid transport medium when its lid is opened, for example when the biopsy sample is introduced into the carrier interior.

Figure 10A:
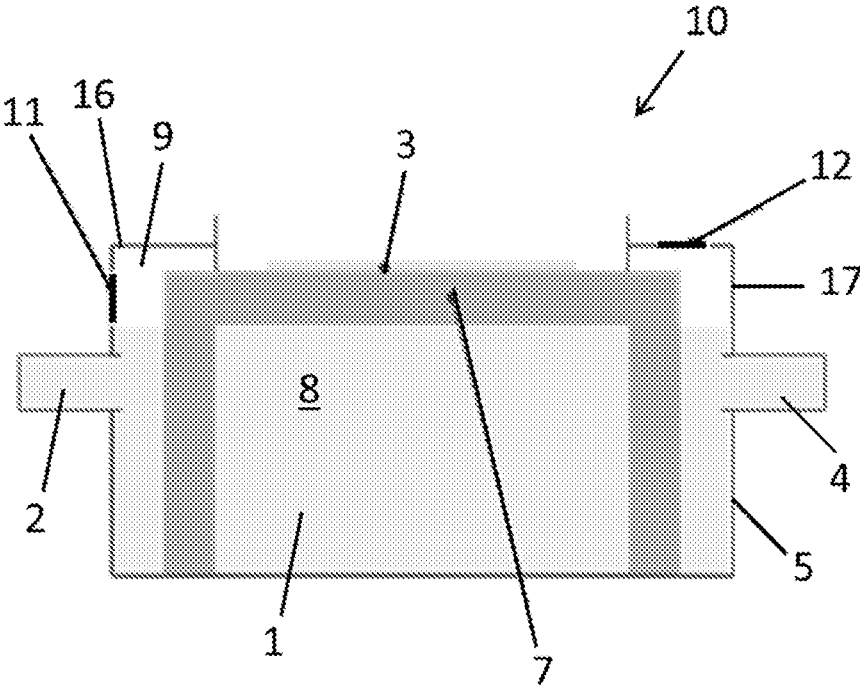
FIG. 10A is a schematic illustration of a biopsy carrier according to an embodiment, shown when positioned in a horizontal orientation and uncovered.
Figure 10B:
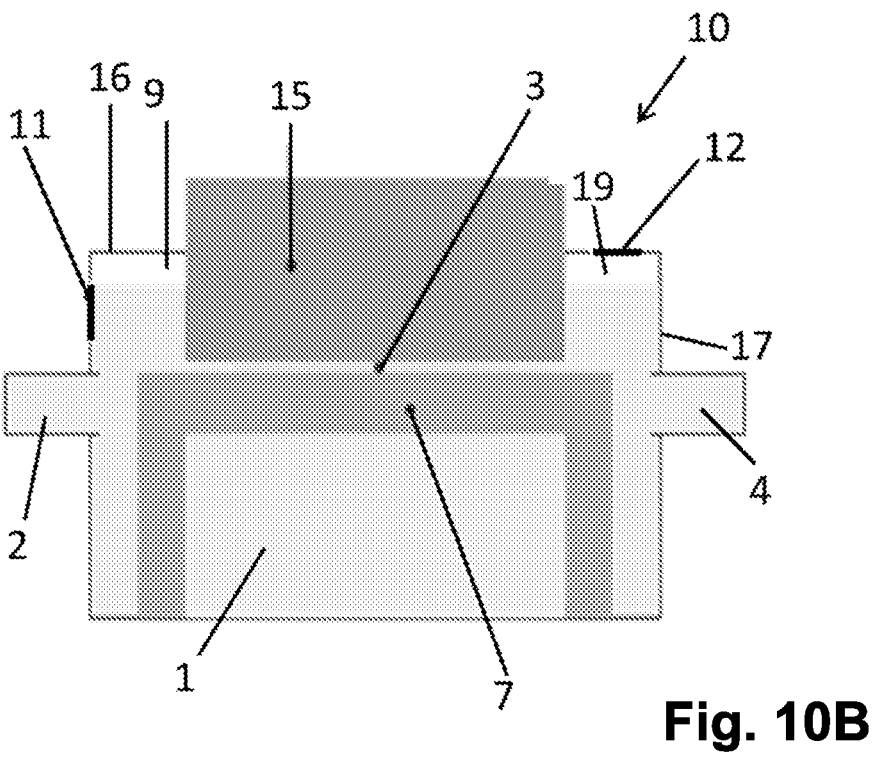
FIG. 10B is a schematic illustration of the carrier of FIG. 10A, shown when positioned in a horizontal orientation and covered.
Figure 10C:
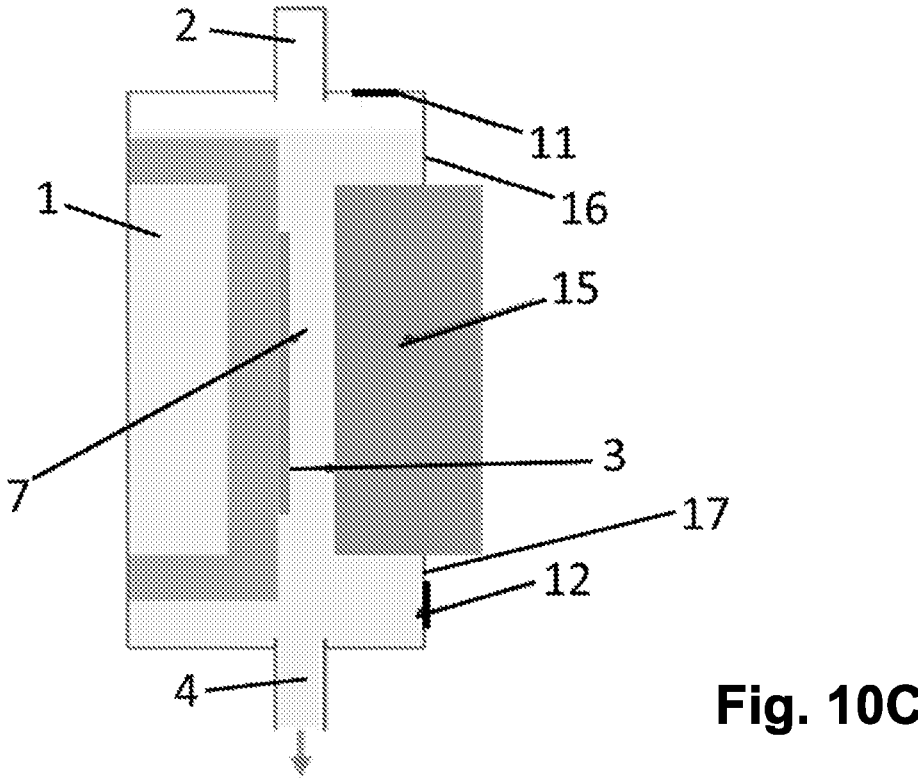
FIG. 10C is a schematic illustration of the carrier of FIG. 10A, shown when positioned in a vertical orientation and covered.

Reference is first made to FIGS. 10A-C, which schematically illustrate inventive aspects of a biopsy carrier 10 in three different stages of operation, respectively.

In FIG. 10A, biopsy carrier 10 provided with a housing 5 and a movable sample support 7 received within the housing is positioned in a horizontal orientation, such that inlet 2 and outlet 4 in liquid communication with housing 5 are laterally spaced from one another. Liquid transport medium 1 is introduced into the housing interior 8 to a level that is above inlet 2 and outlet 4 while providing a void region 9 of air above the transport medium, and support 7 is biased to its normal height which is above the upper surface of transport medium 1 and above inlet 2 and outlet 4. Inlet 2 and outlet 4 are occluded with closures to prevent outward discharge of liquid transport medium 1 therefrom. A biopsy sample 3 is placed on top of support 7. Two spaced venting membranes 11 and 12, which are generally gas permeable and liquid impermeable, cover corresponding small vent openings formed in upper regions 16 and 17, respectively, of housing 5 and in fluid communication with the housing exterior, so as to prevent cross-contamination of biopsy sample 3. At least one of the venting membranes is located above biopsy sample 3.

In FIG. 10B, cover 15 of biopsy carrier 10 is positioned in pressing contact with both biopsy sample 3 and support 7 and in sealing contact with upper regions 16 and 17 of housing 5, thus preventing ingress of contaminating air to biopsy sample 3. Due to the pressing contact of cover 15, support 7 is forced downwardly and liquid transport medium 1 is displaced upwardly, causing air 19 to be expelled through venting membranes 11 and 12 and reducing the size of void region 9. It should be noted that venting membranes 11 and 12 are filtered such that the sterile conditions inside the carrier are not compromised by these membranes. Once cover 15 is removed, support 7 is urged to gradually return to its original position at a height above inlet 2 and outlet 4.

Either support 7 or cover 15 is configured with pre-processing means adapted to pre-process biopsy sample 3, such as by comminution. The pre-processing means are configured to be operational so as to pre-process biopsy sample 3 upon setting cover 15 in pressing contact with both biopsy sample 3 and support 7.

Following pre-processing of biopsy sample 3, biopsy carrier 10 can be repositioned to a vertical orientation as shown in FIG. 10C, such that inlet 2 is located above outlet 4. After the closures of inlet 2 and outlet 4 are removed, a flushing medium is injected into inlet 2 to force the pre-processed biopsy sample together with the transport medium to be downwardly discharged through outlet 4, so as to be received by the laboratory-type equipment. Even though cover 15 is no longer in pressing contact with support 7, the cover remains in sealing contact with upper housing regions 16 and 17, and therefore liquid is discharged only downwardly through outlet 4.

Figure 11:
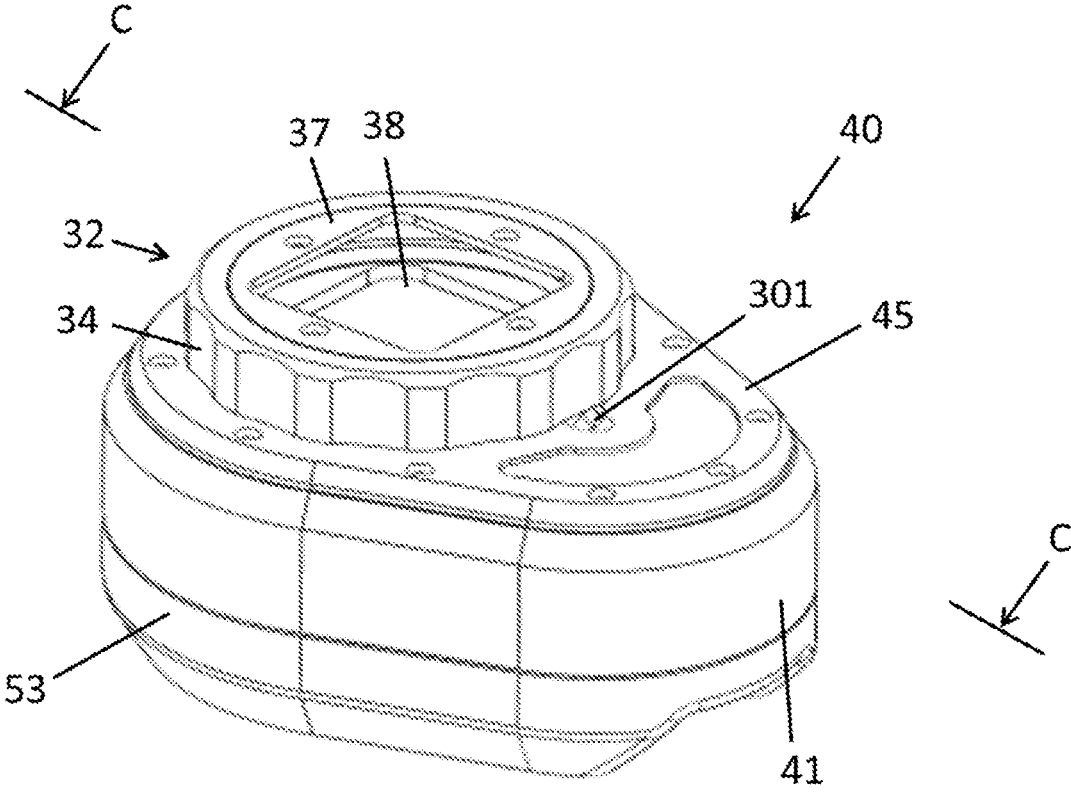
FIG. 11 is a perspective view of a biopsy carrier according to a further specific embodiment, shown when covered.

FIG. 11 illustrates a biopsy carrier 40 provided with at least the same inventive aspects shown in FIGS. 10A-C.

As shown, biopsy carrier 40, which is made of biocompatible materials, comprises a housing member 41, a cover 45 attached to housing member 41, a first relatively small-sized closure 32 releasably attachable to cover 45 for facilitating introduction of the biopsy sample when released, and a second relatively large-sized closure 53 releasably attachable to housing member 41 at a portion thereof that is opposed to first closure 32. First closure 32 may in turn comprise a plurality of elements—for example a threaded ring 34 engageable with a protruding lip of cover 45, a planar window 38 for viewing the biopsy sample, and a holder 37 for window 38. Optionally, when ring 34 is rotated for opening (or closing) closure 32, holder 37 and window 38 are fixed in place. It should be noted, however, that when lifting closure 32 during opening, all of ring 34, holder 37 and window 38 are lifted as a single unit. Venting opening 301 associated with venting membrane 54 (FIG. 14) is also visible.

Optionally, the entire cover 45 may be transparent.

Figure 12:
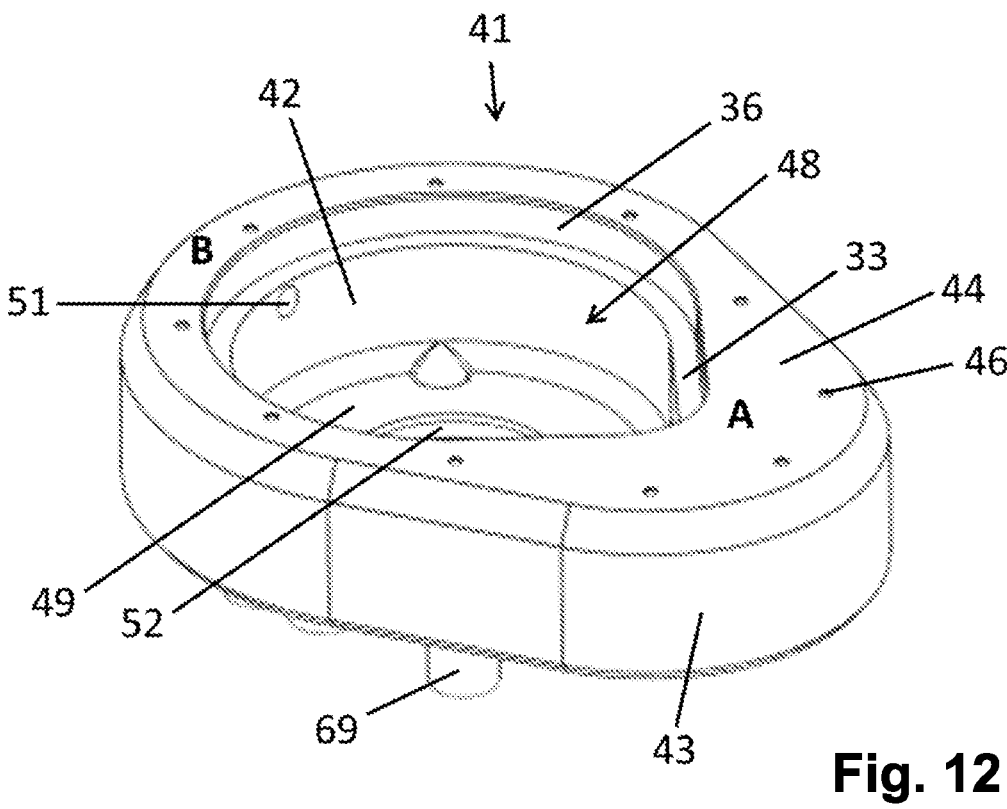
FIG. 12 is a perspective view of a housing member used in conjunction with, and separated from, the carrier of FIG. 11.

As shown in FIG. 12, housing member 41 has a curvilinear peripheral wall 43, although any other shaped peripheral wall is also within the scope of the invention, and a planar support surface 44 substantially perpendicular to peripheral wall 43. Support surface 44 is adapted for connection with cover 45 by a plurality of apertures 46, and may be chamfered to provide a smooth transition to the outer surface of peripheral wall 43.

Housing member 41 is configured with a main cavity 48 recessed from support surface 44 for the insertion therein of a displaceable sample support assembly. A secondary cavity 52 to accommodate a force applier of the sample support assembly may be recessed from a central region of an undersurface 49 of main cavity 48. Spring chambers 69, the purpose of which will be explained below, projecting from undersurface 49 are also visible.

The thickness of peripheral wall 43 at region A of housing member 41 is significantly larger than the thickness of peripheral wall 43 at region B of housing member 41. Region B surrounds main cavity 48 by an angular distance of approximately 200 degrees, while region A surrounds main cavity 48 by the remaining angular distance.

Figure 14:
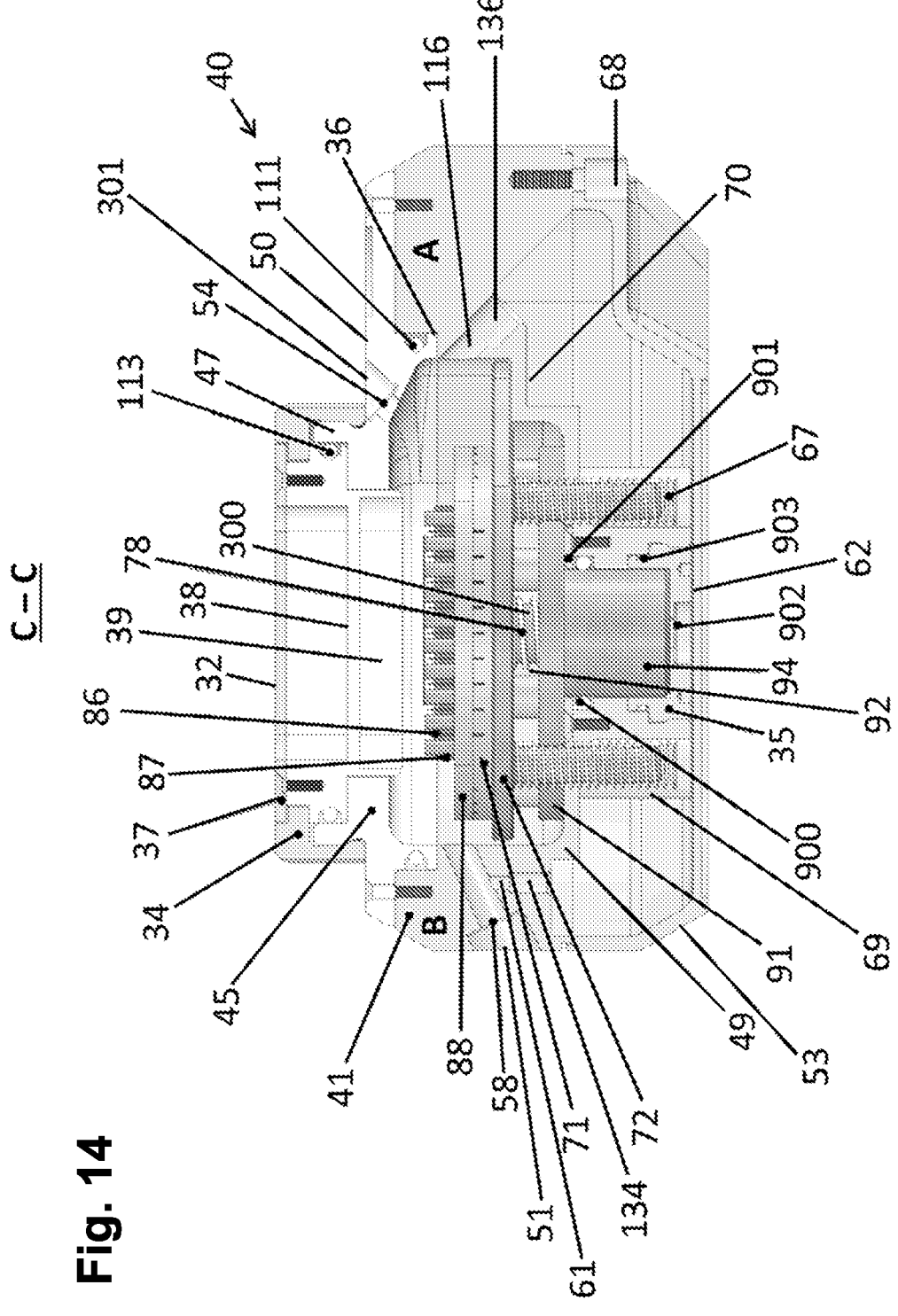
FIG. 14 is a cross-sectional view of the carrier of FIG. 11, taken along the C-C plane of FIG. 11.

To facilitate gas exchange with respect to main cavity 48, a vent opening 51 is formed in region B of peripheral wall 43 and extends to an inner surface 42 of the housing member that delimits main cavity 48, such that vent opening 51 is in fluid communication with both main cavity 48 and the ambient air outwardly from peripheral wall 43. Cross-contamination through vent opening 51 is prevented by means of a gas permeable and liquid impermeable venting membrane 58 (FIG. 14). Vent opening 51 may have two differently sized bores to accommodate venting membrane 58, the latter being sealingly engaged at the interface between the two differently sized bores, such that the larger sized bore is in communication with the ambient air and the smaller sized bore is in communication with main cavity 48.

Housing member 41 may have an additional inner surface 36 that extends substantially perpendicularly from support surface 44 and that is shorter than, and disposed outwardly with respect to inner surface 42. An additional support surface 33 for supporting a complementary element of cover 45 is defined by additional inner surface 36.

An additional fluid passage opening, such as an outlet port 116 in communication with main cavity 48 may be formed in thickened peripheral wall region A of housing member 41.

Figure 15:
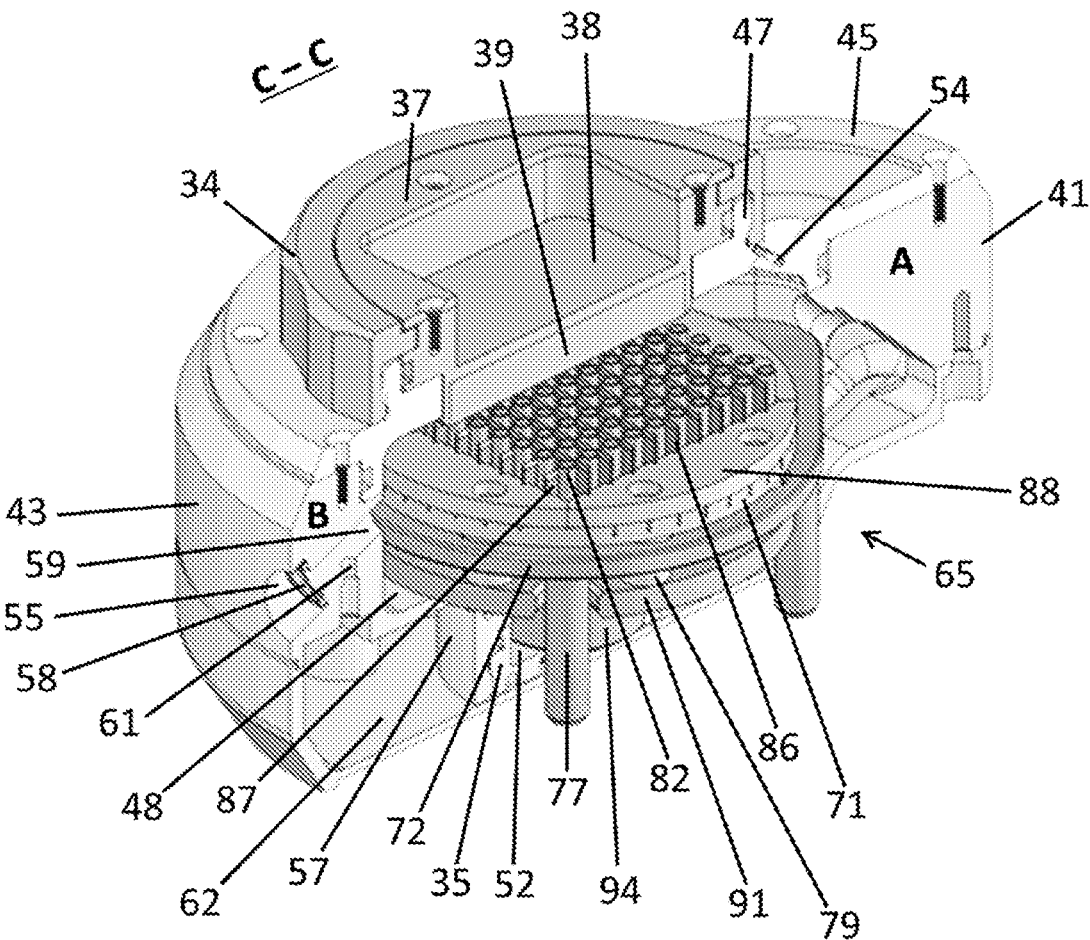
FIG. 15 is a perspective cross-sectional view of the carrier of FIG. 11, taken along the C-C plane of FIG. 11, while a sample support assembly received within its interior is shown in perspective unsectioned view.

As shown in FIG. 15, an inlet port 61 may be in fluid communication with the smaller sized bore 59 of the vent opening, in order to bypass venting membrane 58 fitted in the interface between larger sized bore 55 and smaller sized bore 59 of the vent opening, which is shown to be oblique with respect to the surface of outer peripheral wall 43 through which it is bored.

Figure 13:
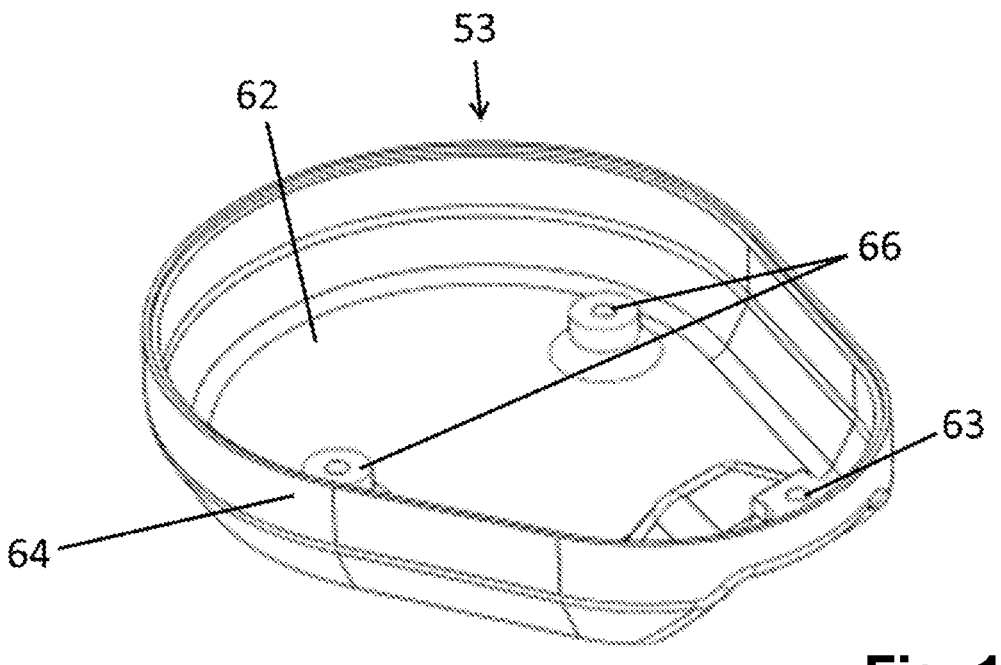
FIG. 13 is a perspective view of a second closure used in conjunction with, and separated from, the carrier of FIG. 11.

Second closure 53 is illustrated in FIG. 13. Second closure 53 has a planar bottom surface 62 and a peripheral wall 64 substantially perpendicular to planar surface 62 that is alignable with the peripheral wall of the housing member throughout its periphery. Second closure 53 is used to cover the operational parts located at the bottom of the carrier, such as the piston and the tubing connected to the inlet and outlet of the main cavity 48 (FIG. 15), thus providing a physical barrier for protecting the valuable operation parts from a mechanical damage on route. As would be appreciated, in order to connect the biopsy carrier to the laboratory-type processing equipment via the inlet and outlet tubes, second closure 53 should first be removed in order to expose said inlet and outlet tubes. Furthermore, in order to pre-process the biopsy sample by way of cutting, both second closure 53 and then cap 35 should be removed in order to gain access to the force applier 94, as will be explained in further details below.

FIG. 14 illustrates a cross sectional view of biopsy carrier 40 when first closure 32 and second closure 53 are attached by a maximum extent to housing member 41. That is, first closure 32 is rotatably and threadedly engageable with annular protruding lip 47 of cover 45, and a plurality of fasteners 68 are used to secure second closure 53 to housing member 41, for example passing through mounting holes 63 and 66 (visible in FIG. 13) formed in second closure 53 and introducible into corresponding mating elements provided with housing member 41 (mating element 66' in housing member 41 for mounting hole 66 is visible in FIG. 27).

When first closure 32 is attached to housing member 41 as shown, and sealing ring 900 is fixated around tubular force applier 94 by seal fixation 901, the main cavity is aseptically closed, such that the cavity is able to undergo gas exchange with the ambient air only via venting membranes: venting membrane 58 provided at unthickened peripheral wall region B, as described above, and via venting membrane 54 sealingly engaged at an interface between two differently sized bores formed in cover 45 at a region adjacent to protruding lip 47 and positioned obliquely with respect to the upper planar surface 50 of cover 45 so as to be in fluid communication with the main cavity. A similar venting membrane 902 is located in cap 35. A cover seal 111 attached to surface 36 of housing member 41 for providing sealing engagement with cover 45 and a lip seal 113 attached to lip 47 of cover 45 for providing sealing engagement with a peripheral portion of sample contactor 39 assist in aseptically closing the main cavity 48. Similarly, a cap seal 903 attached to cap 35 also contributes to the main cavity 48 being aseptically closed.

An outlet port 116, to which outlet tube 136 is connected, is in fluid communication with the main cavity, and may be configured with two differently sized bores and formed in thickened peripheral wall region A of housing member 41. Outlet port 116 may be obliquely positioned with respect to inner surface 42 of housing member 41 close to its junction with support surface 33 (FIG. 12), and extend to one of the multi-level lower surfaces 70 formed in thickened peripheral wall region A.

With reference also to FIG. 15, displaceable sample support assembly 65 is shown to be received within the main cavity 48 of housing member 41. Assembly 65 is able to be received within the main cavity only after cover 45 is removed since the lateral dimension of assembly 65, generally its diameter, is greater than the inner diameter of lip 47.

Figure 16:
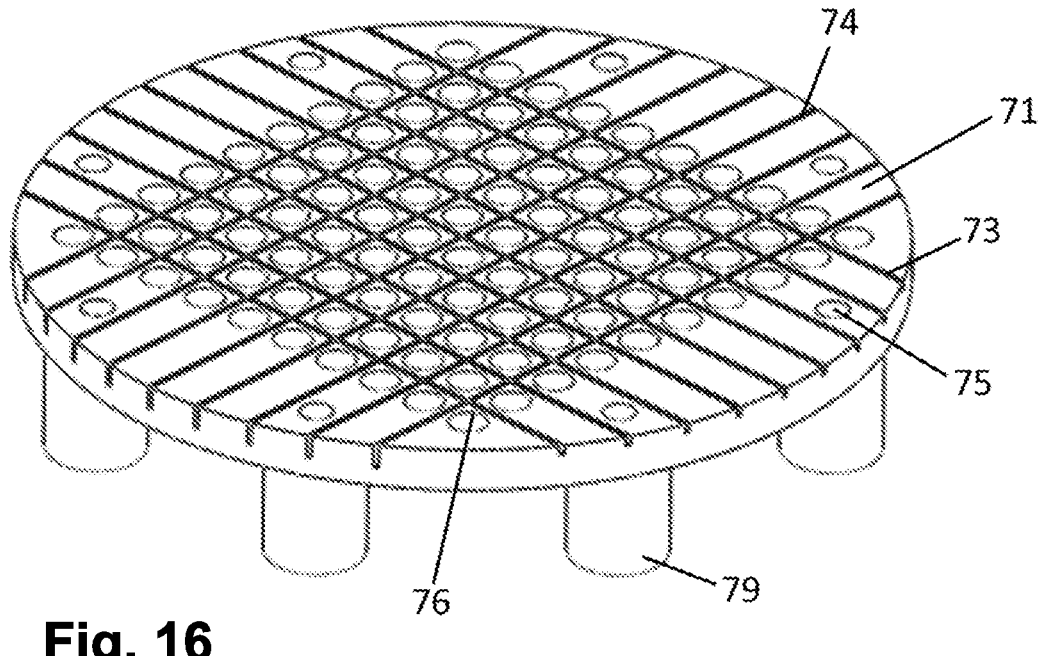
FIG. 16 is a perspective view of a blade support used in conjunction with, and separated from, the carrier of FIG. 11.

Sample support assembly 65 comprises a circular blade support 71, a stripper plate 72, a force transmitting unit 93 and a blade frame 88. Circular blade support 71 having a planar surface which is recessed, as shown in FIG. 16, comprises a plurality of first elongated and mutually parallel blade-receiving slots 73 and a plurality of second elongated and mutually parallel blade-receiving slots 74 that are substantially perpendicular to the first blade-receiving slots 73. Each of the first 73 and second 74 blade-receiving slots extend between two peripheral regions of circular blade support 71. Blade support 71 is also recessed with a plurality of spaced apertures 76 arranged in a rectangular formation, e.g. square. Each aperture 76 is delimited by one or more first 73 and second 74 blade-receiving slots and accommodates an elongated blade guard 82 protruding from stripper plate 72, the purpose of which will be explained below. A plurality of circumferentially spaced legs 79, e.g. eight, extends from the underside of blade support 71.

A first blade 86 is received in each first slot 73, and a second blade 87 is received in each second slot 74, such as by means of a thickened portion of the blade. In order to ensure perpendicularity of first blades 86 and second blades 87, each first blade 86 may be higher than each second blade 87, although shorter than each blade guard 82. Thus each first blade 86 may be slotted, to allow a second blade 87 to be received in aligned blade slots. Other arrangements of interconnected blades are also within the scope of the invention.

Figure 17:
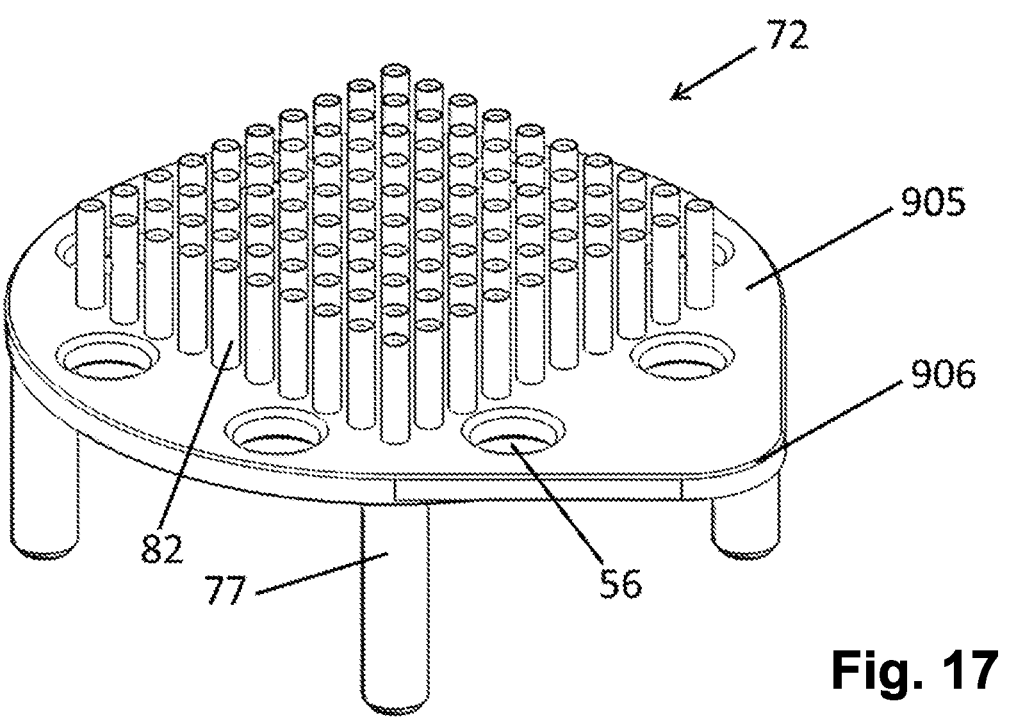
FIG. 17 is a perspective view of a stripper plate used in conjunction with, and separated from, the carrier of FIG. 11.

Stripper plate 72, shown in FIG. 17, comprises a planar plate 905 in abutting relation with, and of a larger diameter than, blade support 71. A plurality of legs 77, e.g. four, extend from the underside of planar plate 905 and are received in corresponding spring chambers 69, within each of which a spring 67 surrounding a leg 77 and adapted to slow the rate of displacement of stripper plate 72 is inserted. A plurality of spaced blade guards 82 of equal length, protruding from planar plate 905, defines a platform on top of which a biopsy sample is placeable. Each aperture 56 bore in stripper plate 72 accommodates blade support leg 79. Planar plate 905 may be circular or may have an asymmetric shape, such that a tip 906 may is in contact with the inner surface of thickened peripheral wall region A, allowing better accommodation of the stripper plate 72 within the main cavity 48. Stripper plate 72 also comprises a central leg 300 (visible in FIGS. 15 and 21), which protrudes from the undersurface of the central region of the planar plate 905 and is received in hollow cavity 92 of the force transmitting unit 93, where it surrounded by center spring 78.

Figure 18:
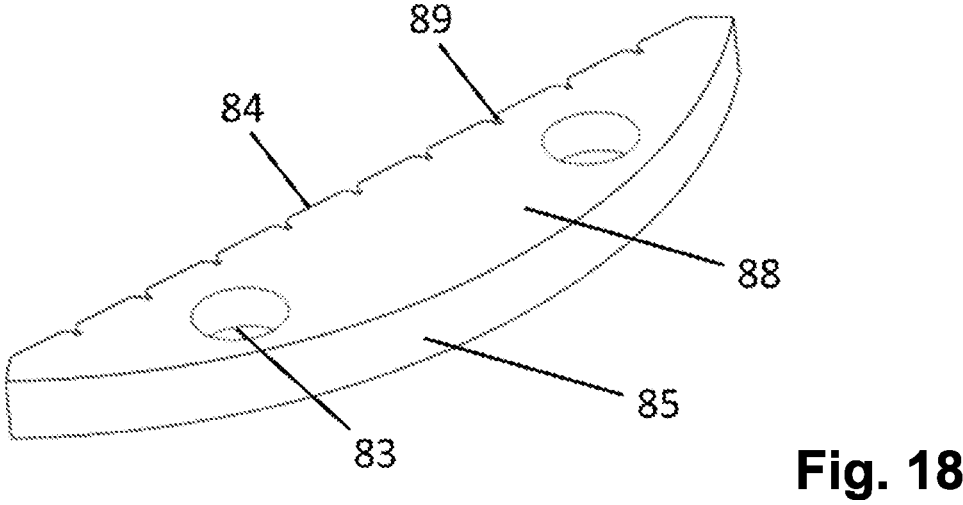
FIG. 18 is a perspective view of a blade frame used in conjunction with, and separated from, the carrier of FIG. 11.

A blade frame 88 is placed in juxtaposition with a corresponding portion of blade support 71 that is positioned radially outwardly from the rectangular apertures formation. As shown in FIG. 18, blade frame 88 has a straight edge 84 formed with a plurality of spaced grooves 89, e.g. V-shaped grooves, each of which adapted to receive the end of a corresponding blade, and a peripheral curved portion 85, generally of the same curvature as the peripheral portion of blade support 71 and aligned therewith.

Four blade frames 88 may be employed, one in juxtaposition with a corresponding radially outwardly positioned portion of blade support 71. Alternatively, a single blade frame having four interconnected sections may be employed, each being identical to blade frame 88.

Figure 19:
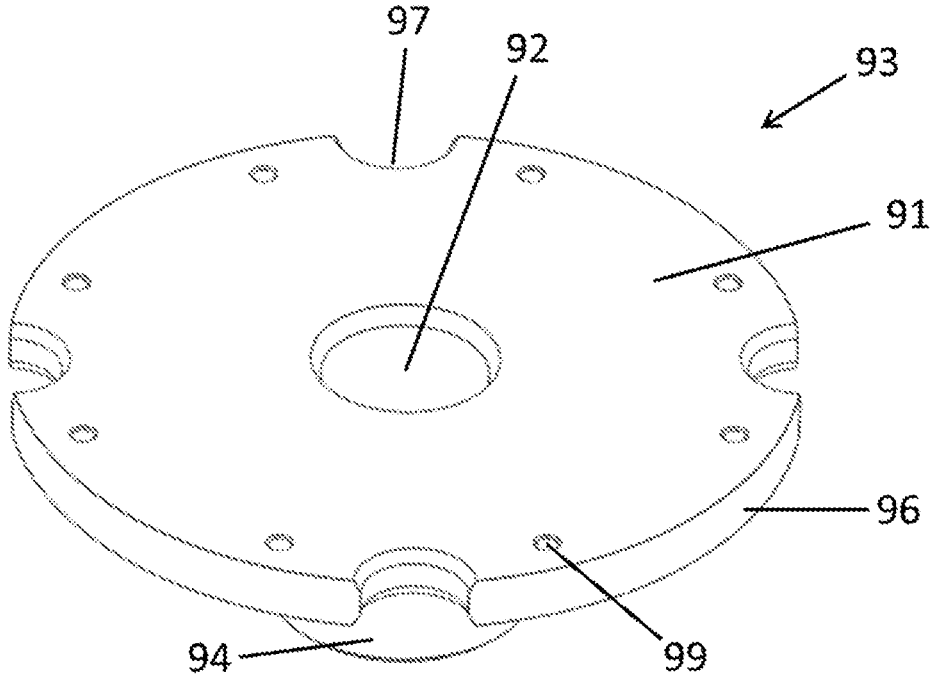
FIG. 19 is a perspective view of a force transmitting unit used in conjunction with, and separated from, the carrier of FIG. 11.

FIG. 19 illustrates a force transmitting unit 93. Force transmitting unit 93 comprises contact plate 91 substantially parallel to the stripper plate and the blade support, and hollow tubular force applier 94, which extends perpendicularly from a central region of the underside of contact plate 91 and is generally of a significantly smaller diameter than that of contact plate 91. The longitudinal axis of the hollow cavity 92 formed within tubular force applier 94 preferably coincides with the center of contact plate 91, allowing the force transmitted by force applier 94 and dampened by center spring 78 received in cavity 92, and generally protruding therefrom until contacting stripper plate 72, to be balanced. The outer edge 96 of contact plate 91 may be formed with a plurality of circumferentially spaced semicircular notches 97, to accommodate the extension therethrough of corresponding stripper plate legs 77. Since spring 78, which surrounds central leg 300 of the stripper plate 72, is compressed during application of compression force to the force transmitting unit 93, spring 78 is elongated back to its resting position after removing the compressing force, thereby causing the force transmitting unit 93 and consequently the blade support 71 to be displaced back into their rested positions.

Each blade frame 88 is fixated to blade support 71, for example by means of an elongated fastener passing through an aperture 83 formed in blade frame 88, a through-hole 75 bored in a corresponding blade support leg 79 and aligned with aperture 83, and a hole 99 aligned with through-hole 75 and which is formed in a region of contact plate 91 that is located between the projection of the outer surface of force applier 94 and outer edge 96 of contact plate 91. The fastener may be secured by well-known means such as threading formed within hole 99.

In the position shown in FIGS. 14 and 15, force applier 94 is received in, and contacted by, hollow cap 35. Hollow cap 35 has a cylinder shape, the bottom of which is a threaded ring engageable with outer wall 57 of secondary cavity 52, thus securing hollow cap 35 in place. Hollow cap 35 may also comprise a groove to accommodate cap seal 903. When cap 35 is secured within cavity 52, force applier 94 is prevented from unintentionally applying force to spring 78 and cause accidental cutting of the biopsy sample by blades 86 and/or 87.

When first closure 32 is fully engaged with annular protruding lip 47 of cover 45, transparent sample contactor 39, which is located below window 38 and may be made of silicone, is in abutting relation with the biopsy sample from the top, while the plurality of blade guards 82 are pressing against the biopsy sample from the bottom, thus immobilizing the biopsy sample during transport. Furthermore, sample contactor 39 acts as a counterpressure during the cutting of the biopsy, such that stripper plate 72 is not displaced by the force applied during the cutting procedure. In addition, blades 86 and/or 87 will pierce through the silicone, allowing a better and complete cutting of the biopsy sample. As would be appreciated, the sample contactor 39 is an integral part of first closure 32, such that removing first closure 32 from the biopsy carrier, sample contactor 39 would also be removed, and the blade array would then be accessible from the top. Sample contactor 39 may be porous or microporous to ensure wetting from the top side of the biopsy sample as well.

With reference to FIGS. 14 and 15, main cavity 48 of housing member 41, in which displaceable sample support assembly 65 is received, is accordingly defined and sealed from above by sample contactor 39 and cover 45, from the sides by peripheral wall regions A and B, and from the bottom by housing member undersurface 49 and sealing ring 900.

Figure 20:
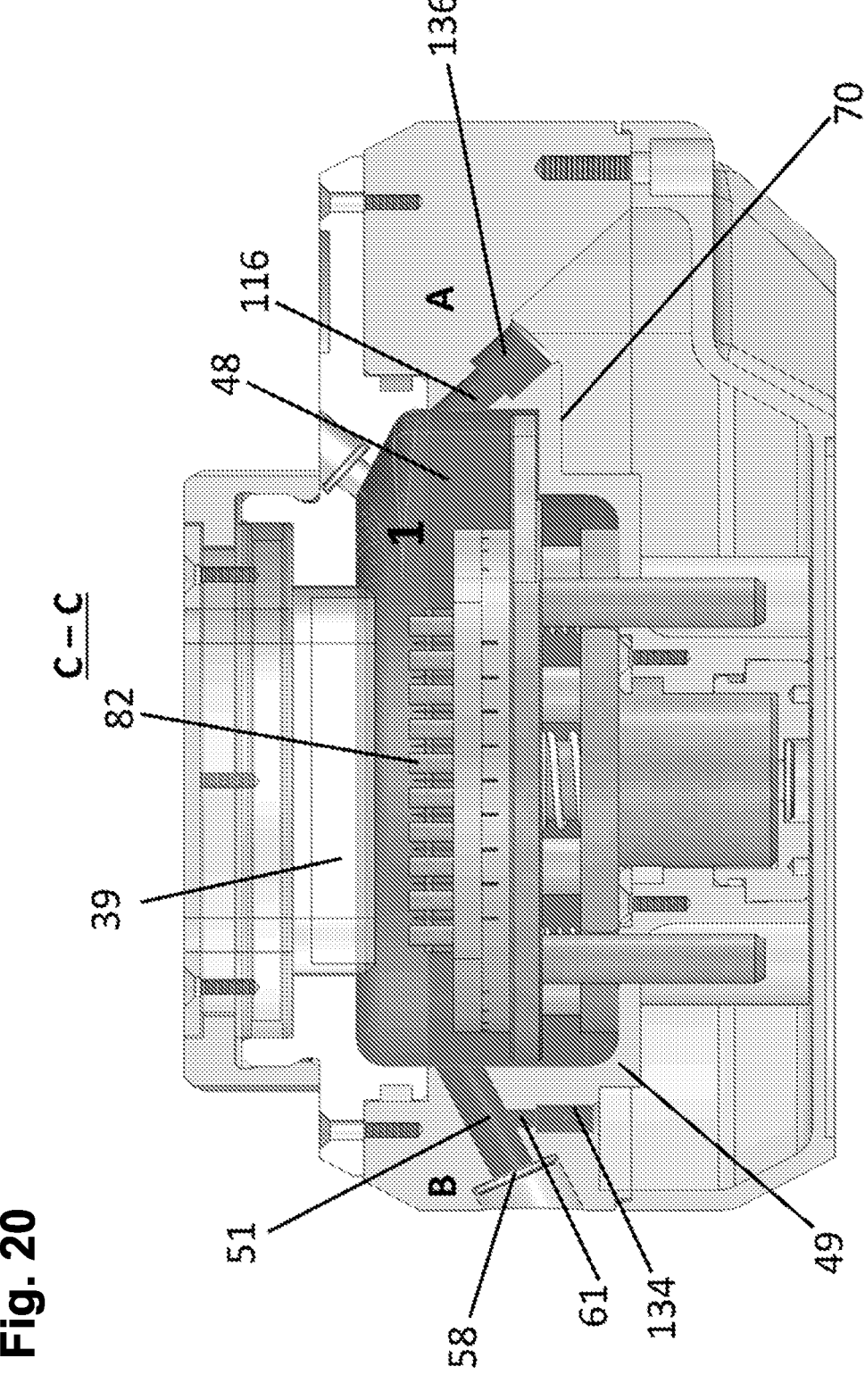
FIG. 20 is a cross-sectional view of the carrier of FIG. 11, taken along the C-C plane of FIG. 11, shown when an aseptically closed cavity thereof is filled with a liquid transport medium.

Accordingly, when main cavity 48 is completely filled with liquid transport medium 1 from housing member undersurface 49 to the level of sample contactor 39 as shown in FIG. 20, all of the blade guards 82 are completely covered by the liquid transport medium. Also, the liquid transport medium flows through opening 51 to venting membrane 58, through inlet port 61 to inlet tube 134, and through outlet port 116 to outlet tube 136. It should be noted that tubes 134 and 136 are closed with a clamp and/or sterile connector to prevent leakage of the transport medium. When main cavity 48 is completely filled with liquid transport medium 1, air is expelled through venting membranes 54 and 58 (FIG. 14).

Figure 21:
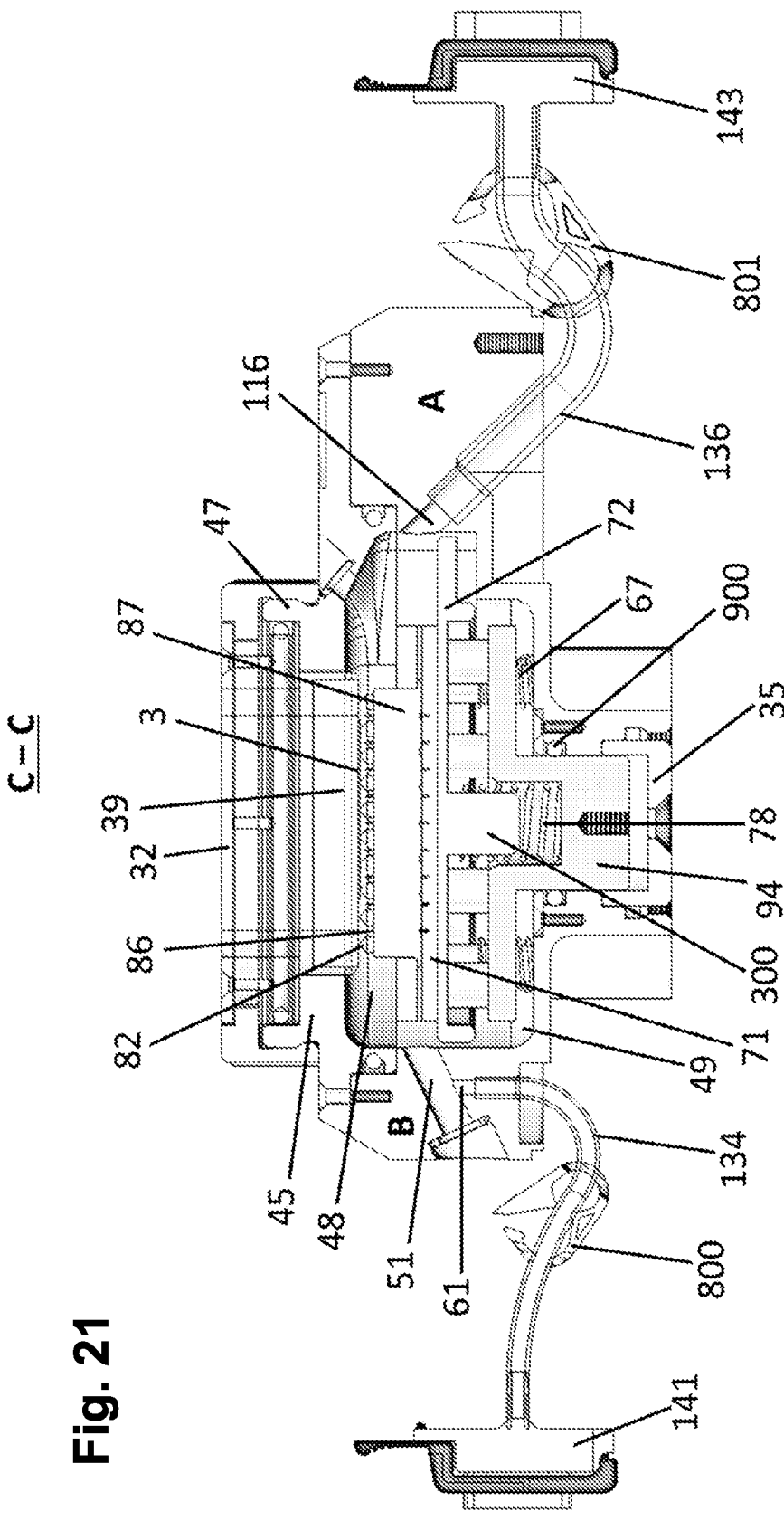
FIG. 21 is a cross-sectional view of the carrier of FIG. 11, taken along the C-C plane of FIG. 11 without the second closure 53, and with inlet and outlet tubing exposed.

FIG. 21 shows a cross-sectional view of biopsy carrier 40 without secondary closure 53, thus revealing inlet tube 134 and outlet tube 136. FIG. 21 clarifies that all parts of the sample support assembly 65, including the force applier 94 and cap 35 which extend below housing member 41, are actually associated with housing member 41 and are not connected to second closure 53. Inlet tube 134 is connected to main cavity 48 through inlet port 61, while outlet tube 136 is connected to main cavity 48 through outlet port 116. Furthermore, in order to prevent leakage of the transport medium from tubes 134 and 136, each of them is secured closed by clamps 800 and 801, respectively. The distal end of inlet tube 134 is attached to sterile connector 141 for facilitating a sterile connection to a source of a flushing liquid. The distal end of outlet tube 136 is similarly attached to sterile connector 143 in order to facilitate a sterile connection to an interface of the laboratory-type equipment.

It should be noted that any commercially available sterile connectors can be used to facilitate connection between the inlet and outlet tubes of the biopsy carrier with their respective connection target. Optionally, tube-welding is also encompassed by the present invention to facilitate a sterile connection between the tubes of the biopsy carrier and their respective connection target.

Figure 22:
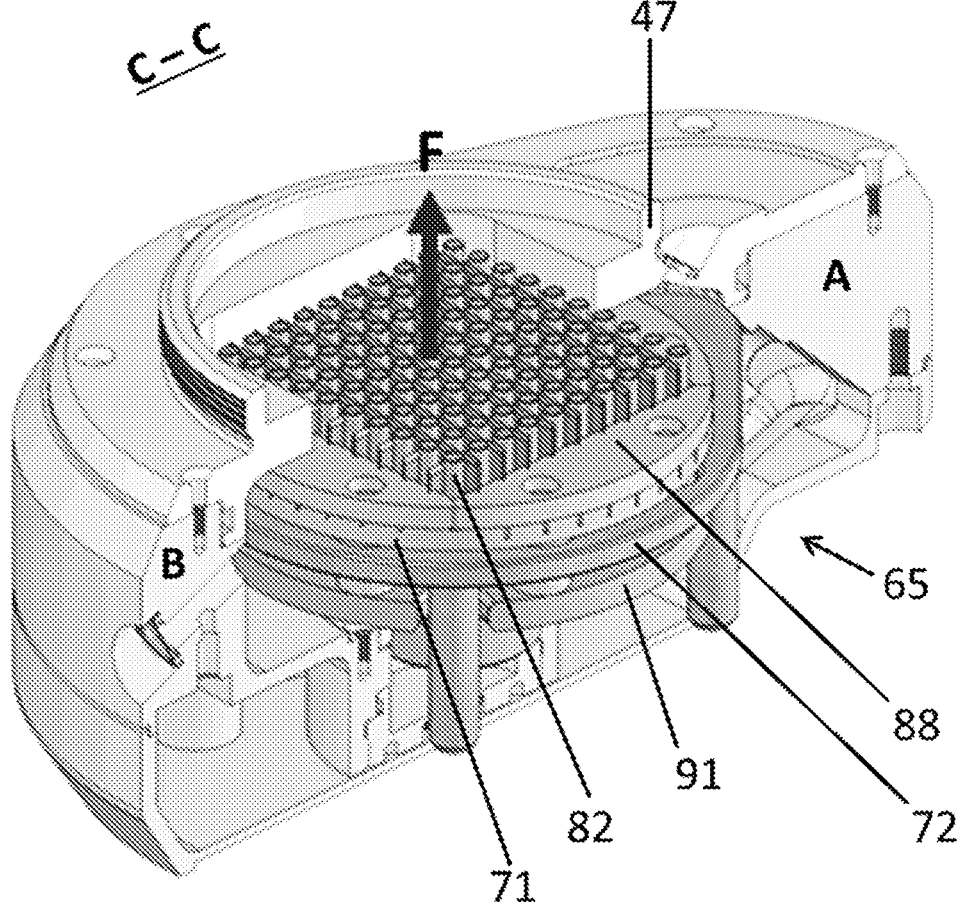
FIG. 22 is a perspective cross-sectional view from the top of the carrier of FIG. 11, schematically illustrating the sample support assembly being upwardly displaced in response to detachment of a first closure therefrom.

When the first closure 32 is removed, as shown in FIG. 22, a compressive force applied by the first closure 32 to sample support assembly 65 is removed, allowing the spring force of springs 67 (FIG. 14) to be released. Springs 67 consequently become extended and apply an upward force F to stripper plate 72. Consequently, stripper plate 72 and blade guards 82 are upwardly and slowly displaced by such a slow rate that ensures that the liquid transport medium will not be spilled from the main cavity. As would be appreciate the rate of upwardly displacing sample support assembly 65 is dependent on the rotation rate of threaded ring 34 when detaching first closure 32.

Figure 23:
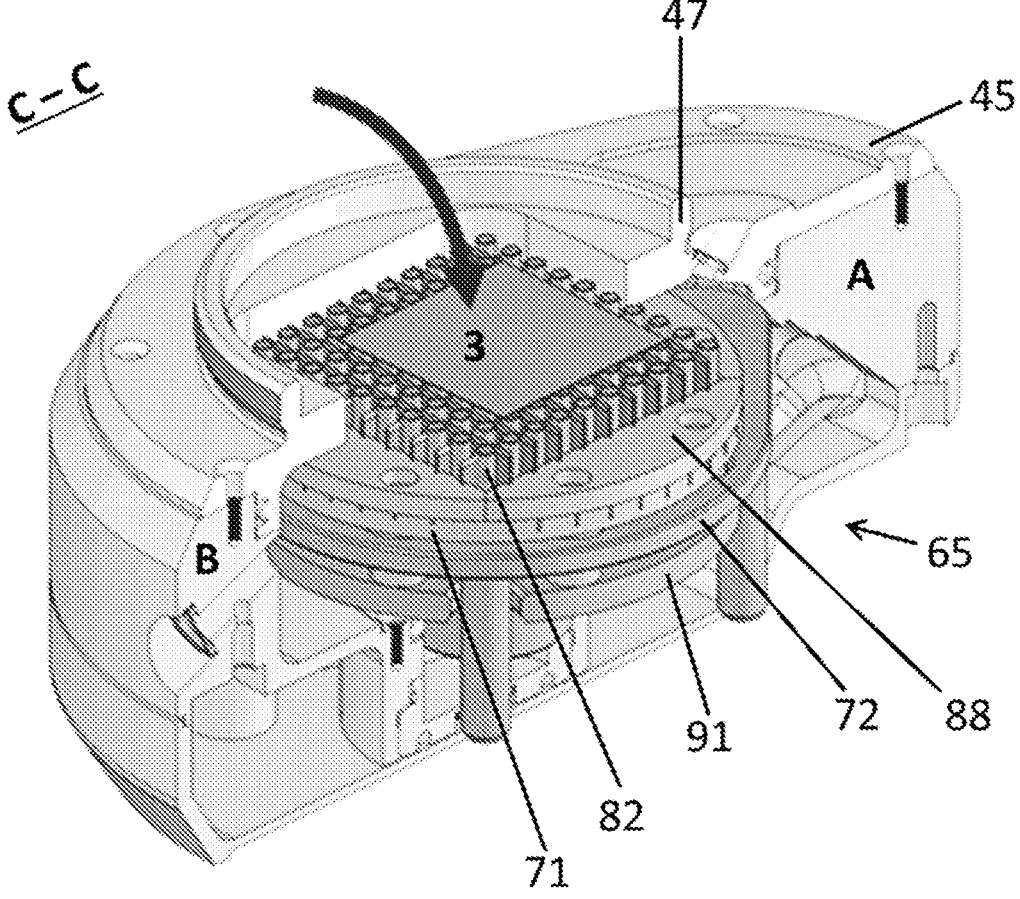
FIG. 23 is a perspective cross-sectional view from the top of the carrier of FIG. 11, schematically illustrating placement of a biopsy sample on top of the sample support assembly.
Figure 24:
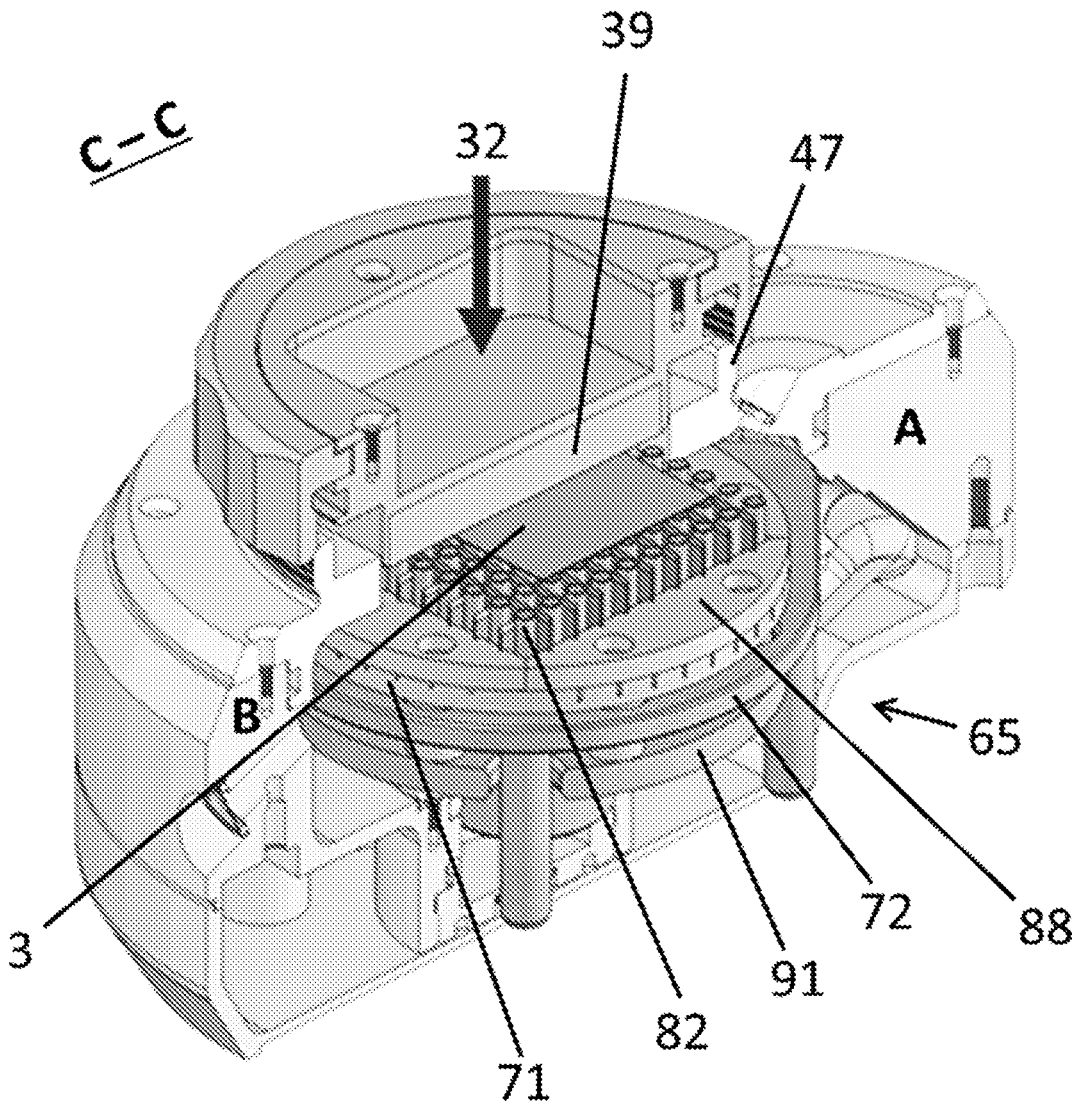
FIG. 24 is a perspective cross-sectional view from the top of the carrier of FIG. 11, schematically illustrating engagement of a first closure therewith.
Figure 25:
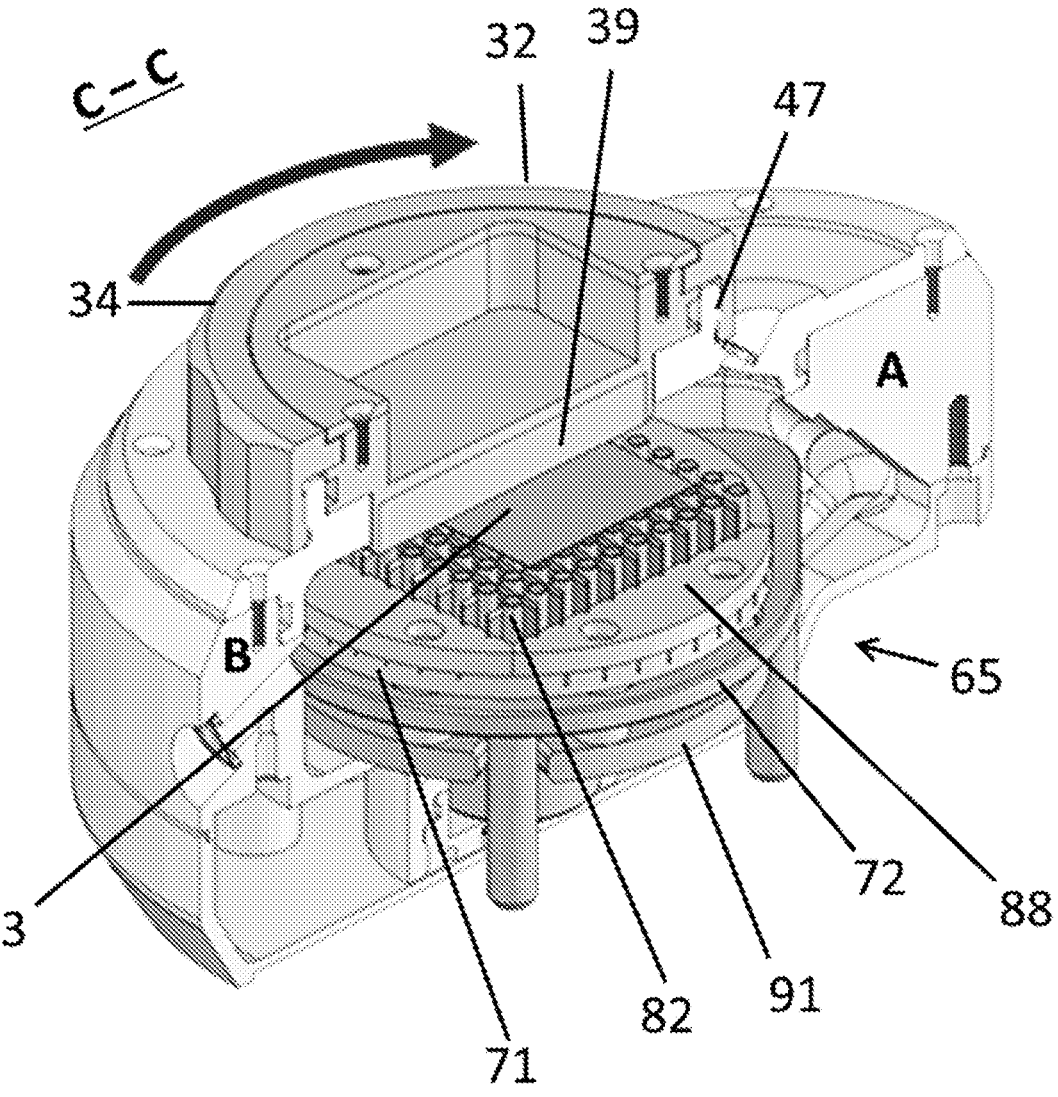
FIG. 25 is a perspective cross-sectional view from the top of the carrier of FIG. 11, schematically illustrating the closing of a first closure with respect to a protruding lip.

After sample support assembly 65 has been successfully raised such that blade frame 88 is in contact with the bottom surface of protruding lip 47, biopsy sample 3 is placed on top of blade guards 82, as shown in FIG. 23. First closure 32 is then lowered on top of protruding lip 47 of cover 45 until positioned in threaded engagement therewith, as shown in FIG. 24. After threaded ring 34 of first closure 32 is rotated to a maximum extent, as shown in FIG. 25, sample contactor 39 is urged to be in pressing contact with biopsy sample 3 while stripper plate 72 and legs 77 force springs 67 to be compressed, thus maintaining biopsy sample 3 submerged in the transport medium even if biopsy carrier 40 is reoriented, for example when the biopsy carrier 40 is set to a vertical orientation or when inverted.

Figure 26:
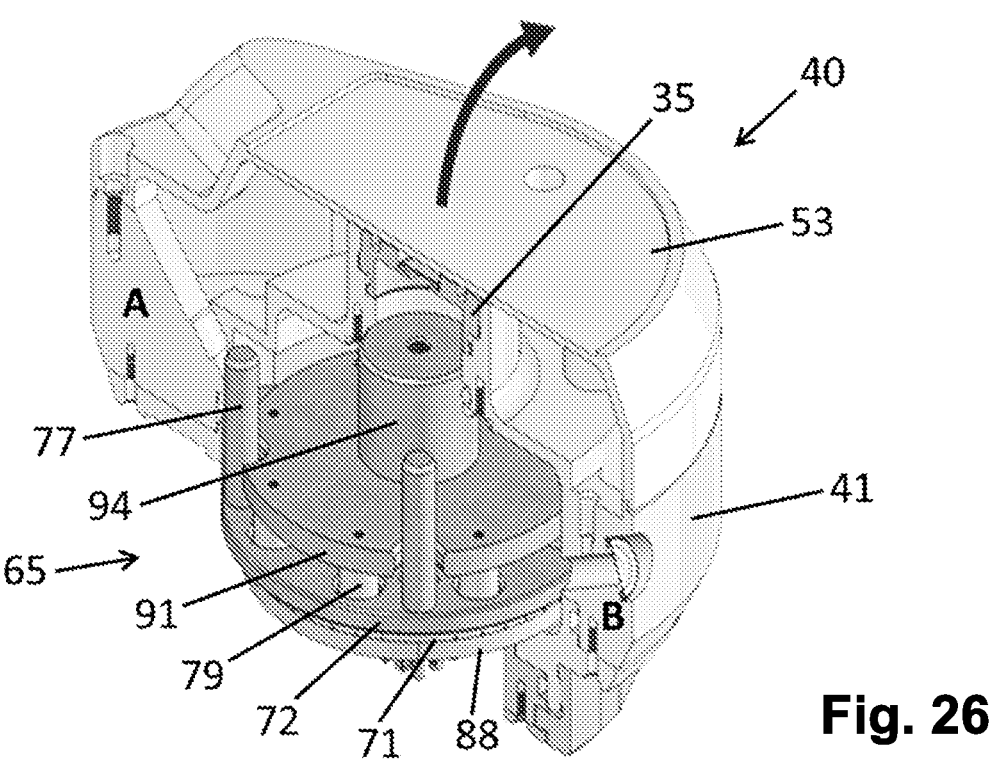
FIG. 26 is a perspective cross-sectional view from the bottom of the carrier of FIG. 11, schematically illustrating detachment of a second closure therefrom.
Figure 27:
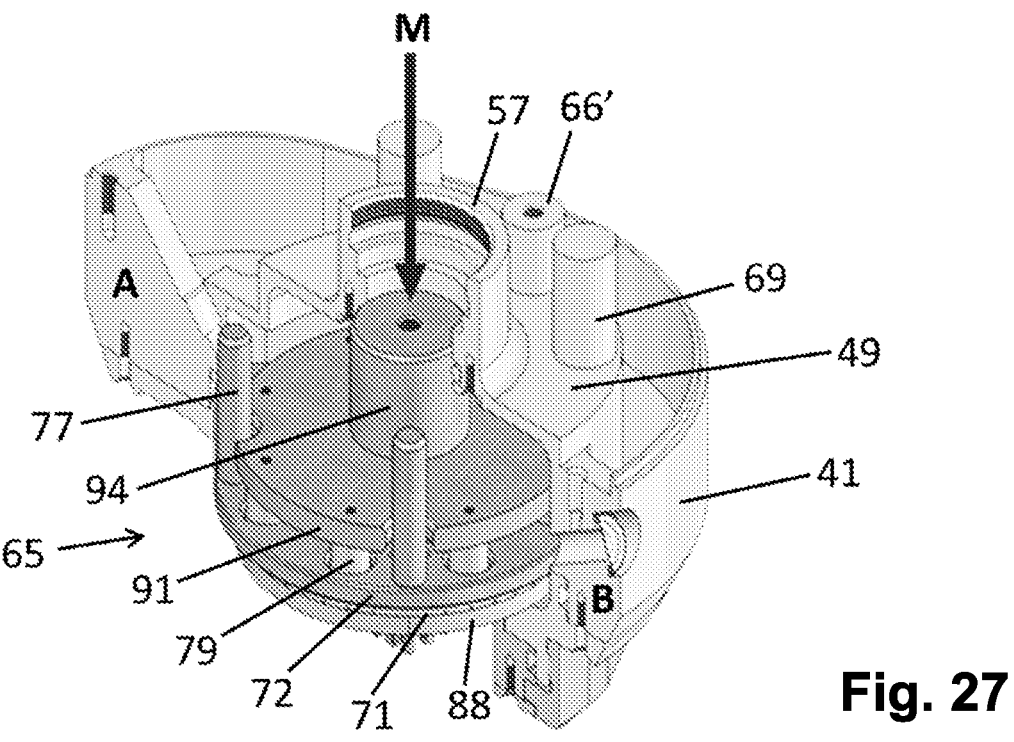
FIG. 27 is a perspective cross-sectional view from the bottom of the carrier of FIG. 11, schematically illustrating linear displacement of the force transmitting unit, the blade support carrying the blade array and the blade frame.
Figure 28:
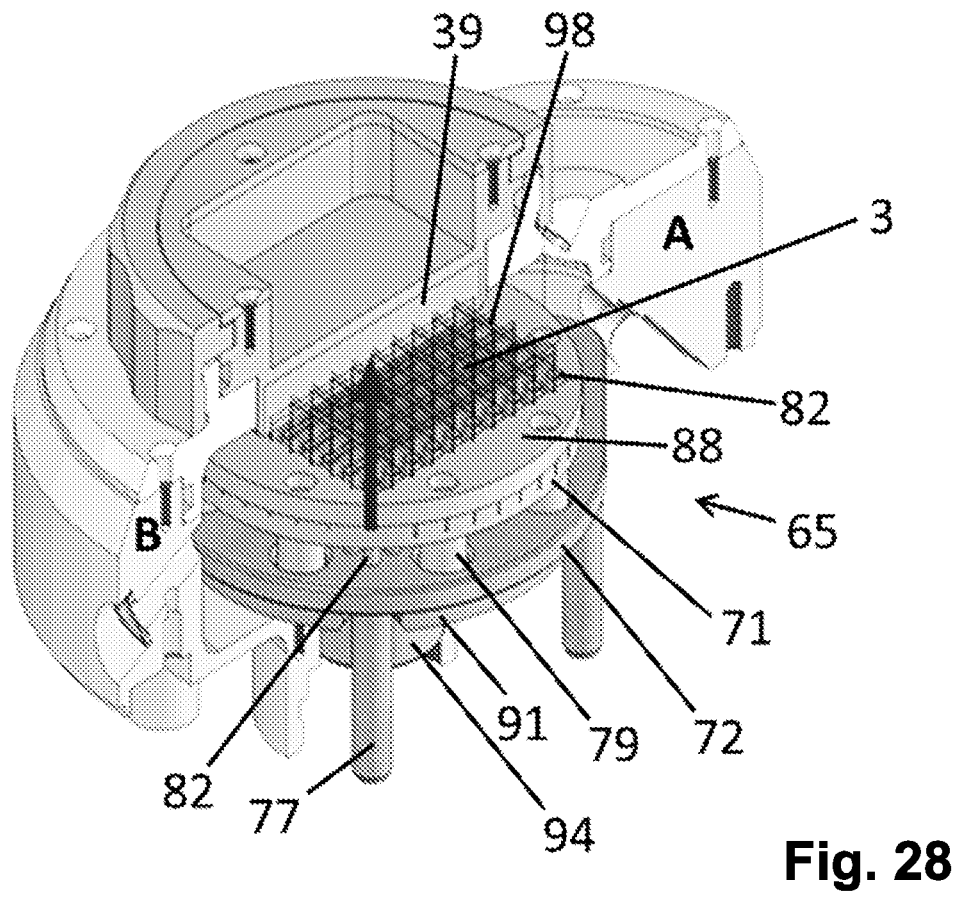
FIG. 28 is a perspective cross-sectional view from the top of the carrier of FIG. 11, schematically illustrating comminution of a biopsy sample.

The procedure illustrated in FIGS. 26-28 is carried out in order to pre-process the biopsy sample by comminution.

Firstly, when biopsy carrier 40 is inverted, for example, whereby force applier 94 is located below second closure 53, as shown in FIG. 26, the second closure 53 is detached from housing member 41, such as by removal of fasteners, and then cap 35 is rotated to be detached from secondary cavity wall 57, thereby gaining access to force applier 94.

An applied manual or automatic force M is then transmitted through the uncovered force applier 94, causing contact plate 91 to push blade support 71 by means of legs 79 away from stripper plate 72 (which remains static due to the counter-pressure on blade guards 82 caused by sample contactor 39 when first closure 32 is fully engaged with cover 45) in the direction of force M, as shown in FIG. 27. During transmission of force M, spring 78, which surrounds central leg 300 of the stripper plate 72, is compressed. Accordingly, when the transmission of force M is ceased, spring 78 is elongated back to its resting position, thereby causing the force transmitting unit 93 and consequently the blade support 71 to be displaced back into their rested positions (as are shown in FIG. 26).

When blade support 71 is displaced to a maximum extent, as shown in FIG. 28, a grid 98 of blades 86 and/or 87 surpasses the blade guards 82, which remain static together with stripper plate 72, in height. Grid 98 of blades thus cuts through biopsy sample 3 and becomes embedded in sample contactor 39.

Figure 29:
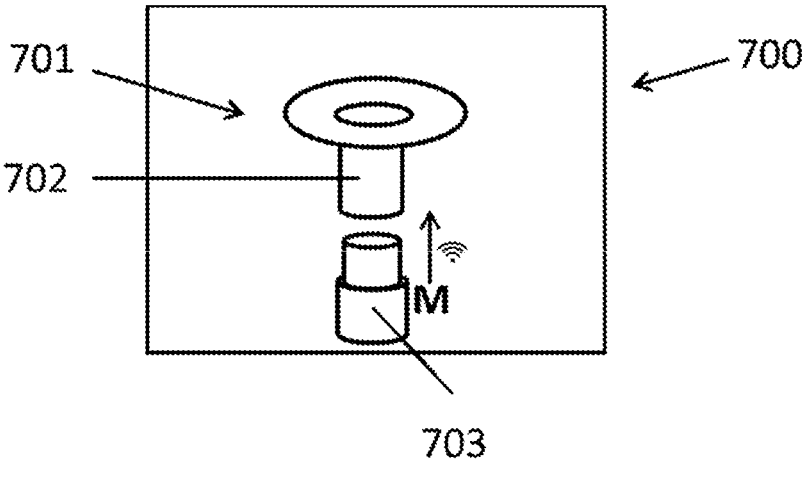
FIG. 29 is a schematic illustration of a biopsy carrier according to an embodiment of the invention, configured with a wirelessly operated piston mechanism.

It should be noted that automatically applying force M may be carried out by wirelessly activating a piston mechanism located between cap 35 and force applier 94. FIG. 29 schematically illustrates a biopsy carrier 700 comprising a force transmitting unit 701 (similar to force transmitting unit 93 of carrier 40), wherein force M is applied by a wirelessly operated piston mechanism 703 located between the bottom of the carrier and force applier 702.

Following pre-processing of the biopsy sample, the biopsy carrier may be advantageously used for aseptically discharging the pre-processed pieces to laboratory-type equipment.

Figure 30:
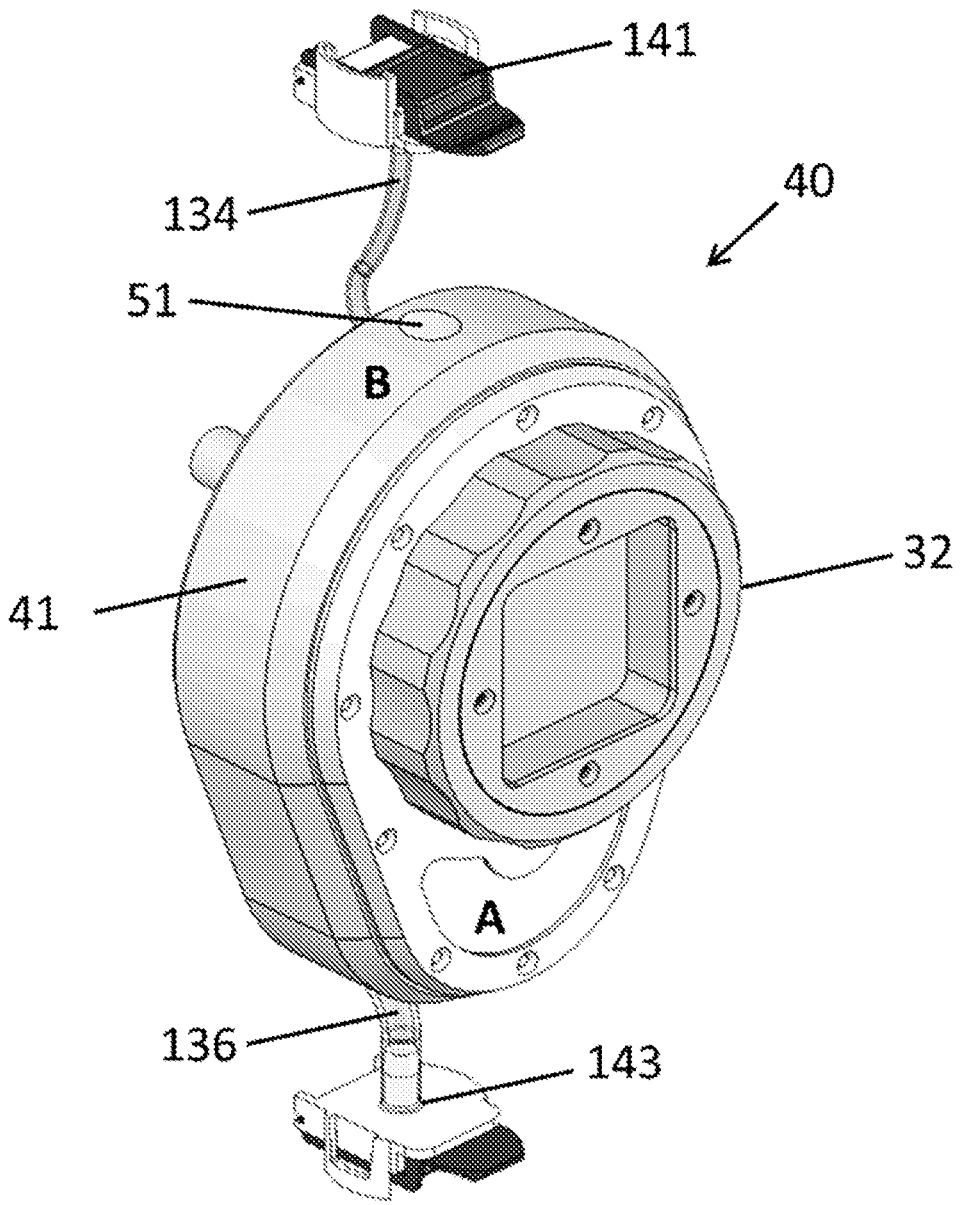
FIG. 30 is a perspective view from the side of the carrier of FIG. 11, when vertically oriented and ready to be connected to laboratory-type equipment through the means of sterile connectors.
Figure 31:
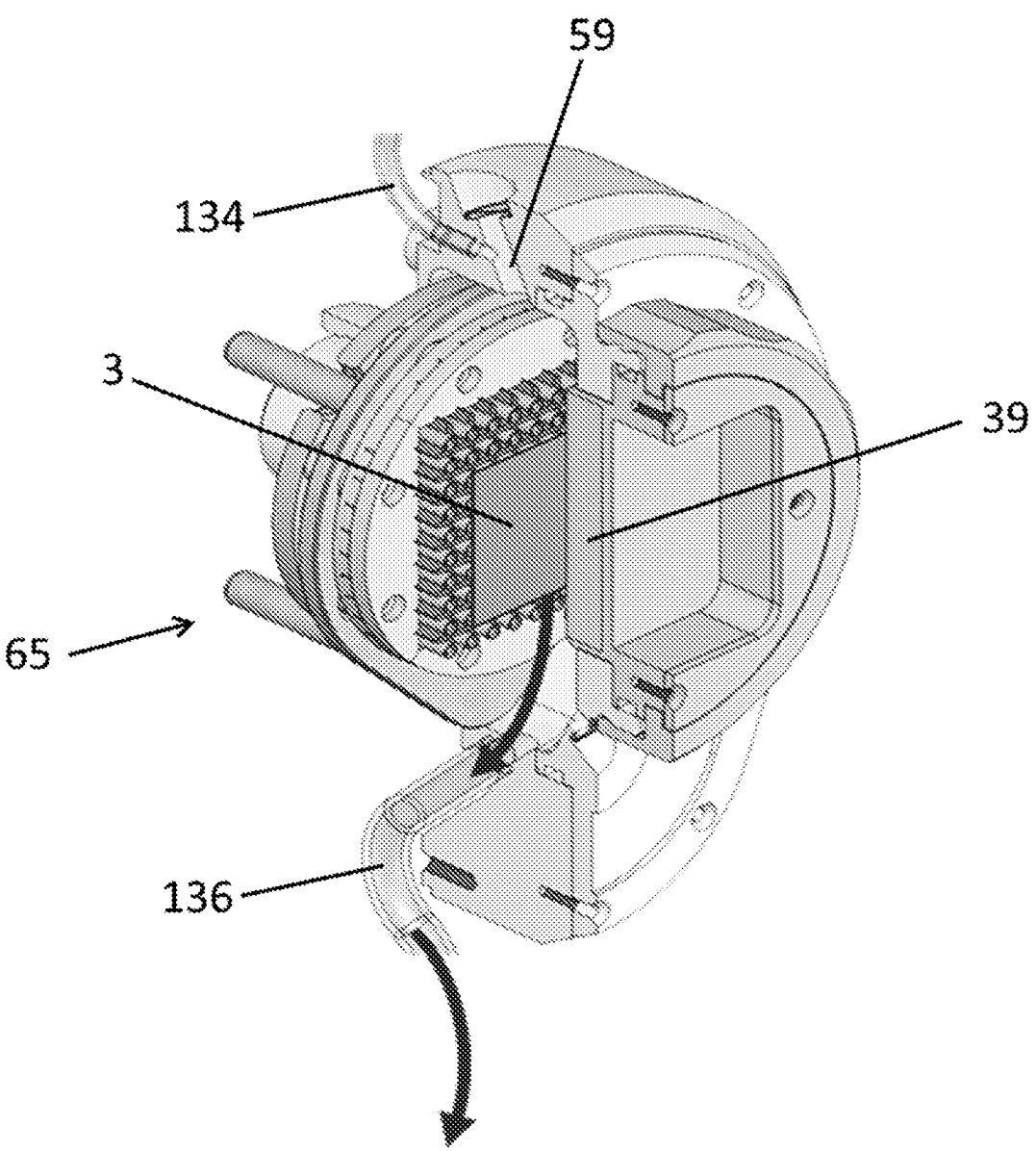
FIG. 31 is a perspective cross-sectional view of the carrier of FIG. 30, schematically illustrating a discharge procedure of the biopsy sample.
Figure 32:
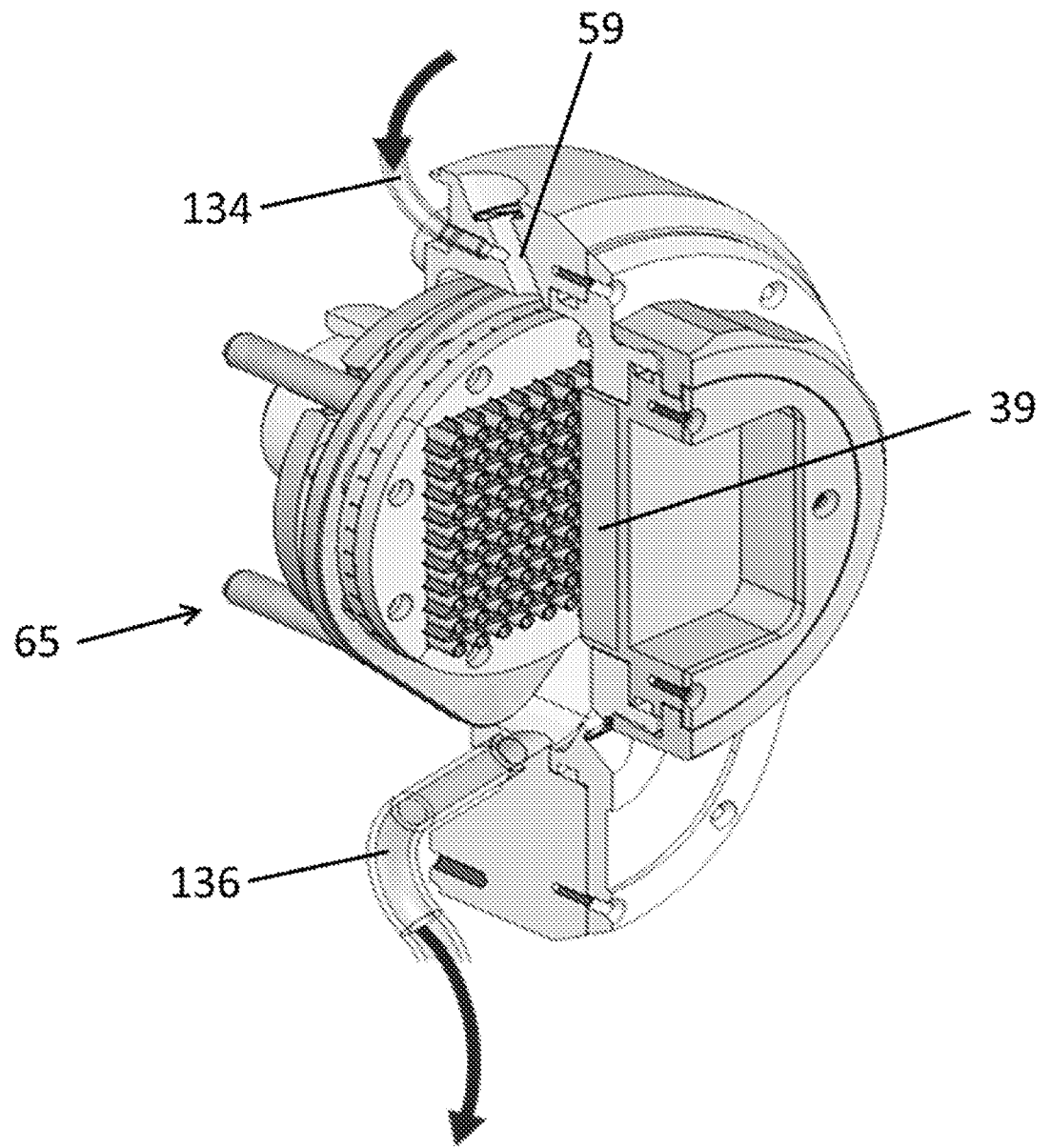
FIG. 32 is a perspective cross-sectional view of the carrier of FIG. 30, schematically illustrating a rinsing procedure.

As shown in FIGS. 30-32, biopsy carrier 40 is set to a vertical orientation whereby unthickened peripheral wall region B is located above thickened peripheral wall region A. As mentioned above, second closure 53 is removed to reveal the inlet tube 134 and outlet tube 136. Since both inlet tube 134 and outlet tube 136 are in fluid communication with the main cavity, a flushing solution introduced through inlet tube 134 will flow into the main cavity and cause pre-processed biopsy pieces, to be flushed through outlet tube 136 and to laboratory-type equipment, whereby the pre-processed biopsy pieces will be further processed. After the main cavity is flushed, it may be rinsed with a rinsing solution, such as culture medium or PBS to ensure that all pieces of the biopsy were flushed out of the carrier.

The laboratory-type equipment to which the pre-processed biopsy pieces are transported may be any type of a tissue processor device, for example, a device for isolation of single cells from tissue samples. The tissue processor device may be automated.

Inlet tube 134 and outlet tube 136 may be connected with sterile connectors 141 and 143, respectively, such as the genderless CPC AseptiQuik® connector to facilitate a connection with an interface of the laboratory-type equipment.

It should be noted that although the embodiments of the biopsy carrier shown in FIGS. 3-32 present both inlet and outlet tubes, the present invention also relates to a biopsy carrier having only an outlet tube (or a plurality of outlet tubes) that is suitable to be connected to a laboratory-type device having a vacuum suction operation in order to cause the biopsy sample to be aseptically discharged from the biopsy carrier. Of course, a suction-facilitated discharge of the biopsy sample may also take place from a biopsy carrier comprising both inlet and outlet tube, whether the inlet tube is connected to a source of flushing liquid or not.

The materials comprising biopsy carrier 40 can be selected according to their biocompatibility, sterilisability and application purpose. For example, housing and structure materials may be made of polycarbonate (PC) or a blend of PC and acrylonitrile butadiene styrene (ABS), components that come in contact with the biopsy sample may be made of biocompatible materials such as polyether ether ketone (PEEK) and polytetrafluoroethylene (PTFE), the blades and springs of the carrier can be made of stainless steel, while silicone can be used for the seals. Venting membranes can be standard 0.2 µm filtered polyethylene terephthalate (PET) or polypropylene (PP) membranes.

The present invention also provides a method for preparing a biopsy sample for subsequent processing operation using the biopsy carrier of the invention, the method comprising:

placing the biopsy sample in the cavity of the biopsy carrier;

immobilizing the biopsy sample by engaging the closure of the biopsy carrier with the structure of the biopsy carrier, thereby:

a. setting the one or more contact elements of the closure in pressing contact with the biopsy sample as well as with the plurality of blades, thereby causing comminution of the biopsy; or b. setting the one or more contact elements of the closure in pressing contact with the biopsy sample as well as with the plurality of blade guards; wherein when the one or more contact elements is set in pressing contact with the biopsy sample as well as with the plurality of blade guards, the method further comprises applying force to the force applier, thereby causing the plurality of blades to cut the biopsy sample into pieces;

connecting the outlet tube of the biopsy carrier to an interface of the laboratory-type equipment and releasing the releasing the closing means from the outlet tube, thereby opening the tube of the biopsy carrier; and causing the biopsy sample through the outlet tube of the biopsy carrier into the laboratory-type equipment.

According to one embodiment, causing discharge of the biopsy sample through the outlet tube is carried out by vacuum suction facilitated by the laboratory device. Alternatively, the method further comprises connecting the inlet tube of the biopsy carrier to a source of flushing liquid and releasing the closing means therefore to open the inlet tube, such that causing discharge of the biopsy sample through the outlet tube into the laboratory-type equipment is carried out by introducing flushing liquid via the inlet tube into the cavity.

It should be noted that the biopsy carrier of the invention is also suitable for transporting a tissue sample, such as a tissue graft, from the laboratory-type equipment to the location where the tissue is to be grafted onto the patient.

All the above description of an embodiment of the invention has been provided for the purpose of illustration, it being understood that the invention is not limited in any way to the specific illustrative embodiment. Many different arrangements of blades and cutting implements can be provided, different flow channels and ways to discharge the comminuted skin can be devised, and many different shapes, sizes and arrangements of the device can be provided by skilled persons, without exceeding the scope of the invention.

The invention claimed is:

1. A biopsy carrier for transporting a biopsy sample, the carrier comprising:

an aseptically closed structure having a cavity prefilled with transport medium;

a selectively sealable and unsealable outlet tube attached to a port in said structure, the port being in fluid communication with the cavity;

wherein, the cavity is configured to receive a biopsy sample such that the biopsy sample is maintained under sterile and wetted conditions while being transported to laboratory-type equipment, thereby maintaining the viability of the biopsy sample;

wherein the biopsy sample is caused to be discharged through the outlet tube to the laboratory-type equipment; and a sample support assembly, the sample support assembly comprises:

a blade support, which is recessed with a plurality of blade-receiving slots within each of which is received a corresponding blade of the plurality of blades and with a plurality of spaced apertures, such that each aperture is delimited by one or more blade-receiving slots; and wherein the blade support comprises a plurality of legs extending from the underside of the blade support;

a stripper plate comprising a planar plate in abutting relation with the underside of said blade support, a plurality of blade guards protruding upwards from the planar plate, each blade guard is accommodated in a corresponding aperture in the blade support, and an aperture accommodating the corresponding leg of the blade support;

a force transmitting unit located beneath the stripper plate and comprising a contact plate, which is set in parallel to the stripper plate and the blade support and is in contact with the plurality of legs of the blade support, and a force applier which extends perpendicularly from the underside of the contact; and optionally a blade frame placed in juxtaposition with a corresponding portion of the blade support that is positioned radially outwardly from the apertures formation of the blade support, the blade frame comprising a plurality of spaced grooves, each of which is configured to receive the end of a corresponding blade, and a peripheral curved portion of the same curvature as the peripheral portion of the blade support and aligned therewith;

wherein when no force is transmitted to the force applier, the blade guards extend higher than the plurality of blades and form a grid onto which the biopsy sample is introduced;

wherein when force is transmitted to the force applier, the contact plate pushes the blade support by means of the plurality of legs away from the stripper plate, in the direction of the transmitted, thus causing the plurality of blades to surpass the plurality of blade guards in height, thereby causing the plurality of blades to cut through the biopsy sample; and wherein the force that is transmitted to the force applier is manually transmitted, or automatically transmitted by a wirelessly operated piston mechanism located between the bottom of the carrier and the force applier.

2. The biopsy carrier according to claim 1, further comprising immobilizing means for protecting the biopsy sample from damage or disfigurement.

3. The biopsy carrier according to claim 1, further comprising a closure and means for displacing the sample support assembly upwardly relative to the structure upon removal of the closure wherein the means for displacing the sample support assembly upwardly relative to the structure comprises a plurality of legs extending from the underside of the planar plate of the stripper plate and chambers configured to receive a corresponding leg of the planar plate; wherein each of the chamber comprises a spring that surrounds the leg of the planar plate;

wherein when the closure is engaged with the structure, a compressive force is applied to the plurality of blade guards, which is transmitted to the stripper plate, thereby causing compression of the springs surrounding the legs of the planar plate; and wherein the springs surrounding the legs of the planar plate are extended to cause displacement of the sample support assembly upon removal of the closure.

4. The biopsy carrier according to claim 3, wherein the closure further comprises one or more contact elements which, following engagement of the closure with the aseptically closed structure, the one or more contact elements are set in pressing contact with both the biopsy sample and the plurality of blade guards to immobilize the biopsy sample.

5. The biopsy carrier according to claim 1, further comprising a selectively sealable and unsealable inlet tube attached to a port in said structure, the port being in fluid communication with the cavity.

6. A method for aseptically transporting a biopsy sample using the biopsy carrier of claim 5, the method comprising:

prefilling the biopsy carrier with transport medium, while the inlet and outlet tubes connected to the biopsy carrier are secured by closing means;

placing a biopsy sample in a cavity of the biopsy carrier;

transporting the biopsy carrier to a laboratory-type equipment;

connecting the outlet tube of the biopsy carrier to an interface of the laboratory-type equipment;

releasing the closing means from the outlet tube of the biopsy carrier, thereby opening the outlet tube of the biopsy carrier; and causing discharge of the biopsy sample via the outlet tube into the laboratory-type equipment.

7. The method according to claim 6, wherein causing discharge of the biopsy sample via the outlet tube into the laboratory-type equipment is carried out by suction facilitated by the laboratory-type equipment.

8. The method of claim 6, wherein prior to causing discharge of the biopsy sample via the outlet tube into the laboratory-type equipment, the method further comprises connecting the inlet tube of the biopsy carrier to a source of a flushing liquid and releasing the closing means from the inlet tube of the biopsy carrier, thereby opening the inlet tube of the biopsy carrier; and wherein causing discharge of the biopsy sample via the outlet tube into the laboratory-type equipment is carried out by introducing flushing liquid via the inlet tube into the cavity.

9. The method according to claim 6, further comprising pre-processing the biopsy sample prior to discharging the biopsy sample via the outlet tube into the laboratory-type equipment.

10. A method for preparing a biopsy sample for subsequent processing operation using the biopsy carrier of claim 6, the method comprising:

placing the biopsy sample in the cavity of the biopsy carrier;

immobilizing the biopsy sample by engaging the closure of the biopsy carrier with the structure of the biopsy carrier, thereby:

a. setting the one or more contact elements of the closure in pressing contact with the biopsy sample as well as with the plurality of blades, thereby causing comminution of the biopsy; or b. setting the one or more contact elements of the closure in pressing contact with the biopsy sample as well as with the plurality of blade guards; wherein when the one or more contact elements is set in pressing contact with the biopsy sample as well as with the plurality of blade guards, the method further comprises applying force to the force applier, thereby causing the plurality of blades to cut the biopsy sample into pieces;

connecting the outlet tube of the biopsy carrier to an interface of the laboratory-type equipment and releasing the closing means from the outlet tube, thereby opening the tube of the biopsy carrier; and causing the biopsy sample to be discharged through the outlet tube of the biopsy carrier into the laboratory-type equipment.

11. The method according to claim 10, wherein causing the biopsy sample to be discharged through the outlet tube of the biopsy carrier into the laboratory-type equipment is carried out by suction facilitated by the laboratory-type equipment.

12. The method according to claim 10, wherein prior to causing discharge of the biopsy sample via the outlet tube into the laboratory-type equipment, the method further comprises connecting the inlet tube of the biopsy carrier to a source of a flushing liquid and releasing the closing means from the inlet tube of the biopsy carrier, thereby opening the inlet tube of the biopsy carrier; and wherein causing discharge of the biopsy sample via the outlet tube into the laboratory-type equipment is carried out by introducing the flushing liquid via the inlet tube into the cavity.

13. A biopsy carrier for transporting a biopsy sample, the carrier comprising:

an aseptically closed structure having a cavity prefilled with transport medium;

a selectively sealable and unsealable outlet tube attached to a port in said structure, the port being in fluid communication with the cavity;

wherein, the cavity is configured to receive a biopsy sample such that the biopsy sample is maintained under sterile and wetted conditions while being transported to laboratory-type equipment, thereby maintaining the viability of the biopsy sample; and wherein the biopsy sample is caused to be discharged through the outlet tube to the laboratory-type equipment;

one or more pre-processing elements, for pre-processing the biopsy sample prior to the discharging of the biopsy sample to the laboratory-type equipment, wherein the one or more pre-processing elements is selected from at least one of:

a plurality of blades for cutting the biopsy sample into pieces;

one or more nozzles for introducing liquid to the biopsy sample, wherein the liquid is a washing solution, a disinfecting solution, a solution comprising a reagent or a buffer;

one or more additional ports for introducing liquid to the biopsy sample, wherein the liquid is a washing solution, a disinfecting solution, a solution comprising a reagent or a buffer;

one or more additional ports for extracting liquid from the cavity of the biopsy carrier;

one or more micro-needles for conditioning the surface of the biopsy sample;

one or more sensors for measuring the pH, dissolved oxygen, biochemistry components and/or the temperature of the liquid inside the cavity;

a bacteria test component; and a transparent part allowing visual contact with the biopsy sample by an imager;

one or more contact elements which, following motion between the one or more contact elements relative to the plurality of blades, are set in pressing contact with both the biopsy sample and the plurality of blades to cause comminution of the biopsy sample and to immobilize the biopsy sample;

a closure carrying the one or more contact elements and which is in releasable engagement with the aseptically closed structure, to occlude cavity; wherein engagement of the closure with the structure causes the one or more contact elements to be set in pressing contact with both the biopsy sample and the plurality of blades.

14. The biopsy carrier according to claim 13, wherein the closure is provided with two or more guides, and the body member is provided with two or more guide rails, each of the rails adapted to receive a guide slidable therein, and the structure is provided with a thermoplastic elastomer configured to undergo deformation when the closure is engaged with the structure.

15. A biopsy carrier for transporting a biopsy sample, the carrier comprising:

an aseptically closed structure having a cavity prefilled with transport medium;

a selectively sealable and unsealable outlet tube attached to a port in said structure, the port being in fluid communication with the cavity;

wherein, the cavity is configured to receive a biopsy sample such that the biopsy sample is maintained under sterile and wetted conditions while being transported to laboratory-type equipment, thereby maintaining the viability of the biopsy sample; and wherein the biopsy sample is caused to be discharged through the outlet tube to the laboratory-type equipment;

one or more pre-processing elements, for pre-processing the biopsy sample prior to the discharging of the biopsy sample to the laboratory-type equipment;

wherein the one or more pre-processing elements is selected from at least one of:

a plurality of blades for cutting the biopsy sample into pieces;

one or more nozzles for introducing liquid to the biopsy sample, wherein the liquid is a washing solution, a disinfecting solution, a solution comprising a reagent or a buffer;

one or more additional ports for introducing liquid to the biopsy sample, wherein the liquid is a washing solution, a disinfecting solution, a solution comprising a reagent or a buffer;

one or more additional ports for extracting liquid from the cavity of the biopsy carrier;

one or more micro-needles for conditioning the surface of the biopsy sample;

one or more sensors for measuring the pH, dissolved oxygen, biochemistry components and/or the temperature of the liquid inside the cavity;

a bacteria test component; and a transparent part allowing visual contact with the biopsy sample by an imager;

one or more contact elements which, following motion between the one or more contact elements relative to the plurality of blades, are set in pressing contact with both the biopsy sample and the plurality of blades to cause comminution of the biopsy sample and to immobilize the biopsy sample;

wherein the one or more contact elements are a plurality of protrusions formed in a releasable closure, and the plurality of blades are fixed to a body member associated with the structure.

* * * * *